(12) United States Patent
Zhao

(10) Patent No.: US 9,101,726 B2
(45) Date of Patent: Aug. 11, 2015

(54) STEM CELL IMMUNE MODULATION METHODS OF USE AND APPARATUS

(75) Inventor: Yong Zhao, Lisle, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 13/514,694

(22) PCT Filed: Dec. 8, 2010

(86) PCT No.: PCT/US2010/059522
§ 371 (c)(1),
(2), (4) Date: Jul. 19, 2012

(87) PCT Pub. No.: WO2011/087637
PCT Pub. Date: Jul. 21, 2011

(65) Prior Publication Data
US 2012/0277652 A1    Nov. 1, 2012

Related U.S. Application Data

(60) Provisional application No. 61/283,782, filed on Dec. 8, 2009, provisional application No. 61/283,810, filed on Dec. 8, 2009.

(51) Int. Cl.
*A61M 37/00* (2006.01)
*A61M 1/34* (2006.01)
(Continued)

(52) U.S. Cl.
CPC ............ *A61M 1/3489* (2014.02); *A61M 1/3472* (2013.01); *C12M 25/08* (2013.01); *C12M 35/08* (2013.01); *C12N 5/0634* (2013.01); *A61K 2035/122* (2013.01); *A61M 2202/0407* (2013.01); *C12N 2502/11* (2013.01)

(58) Field of Classification Search
CPC ............ A61K 45/05; A61K 2035/122; A61M 1/3496; A61M 1/34; A61M 2001/362; A61M 1/3489
See application file for complete search history.

(56) References Cited

U.S. PATENT DOCUMENTS 6,607,501 B2 * 8/2003 Gorsuch ...................... 604/5.01
6,676,622 B2 * 1/2004 Strahilevitz .................. 604/5.01
(Continued)

OTHER PUBLICATIONS

Yong Zhao, Zhihua Huang, Meirigeng Qi, Ping Lazzarini, Theodore Mazzone, Immune regulation of T lymphocyte by a newly characterized human umbilical cord blood stem cell, 108 Immunology Letters, 78-87 (2006).*
(Continued)

*Primary Examiner* — Leslie Deak
(74) *Attorney, Agent, or Firm* — Weisun Rao; Greenberg Traurig, LLP

(57) ABSTRACT

Methods and apparatus are disclosed co-culturing stem cells with mononuclear cells and/or lymphocytes to modulate their function. The invention also discloses the use of stem cells to educate autoreactive immune cells as a mechanism to treat autoimmune diseases and immune disorder-related diseases, such as diabetes. In one aspect of the invention, bioreactors are disclosed closed for modulating lymphocytes and suppressing autoreactive T cells. The bioreactors can include a chamber having at least one positively charged and/or hydrophobic substrate surface, a population of stem cells attached to the substrate surface, an inlet conduit for introducing lymphocytes into the chamber, and an outlet conduit for extracting treated lymphocytes following co-culturing with the stem cells.

54 Claims, 15 Drawing Sheets

(51) Int. Cl.
  *C12N 5/078* (2010.01)
  *C12M 1/12* (2006.01)
  *C12M 1/42* (2006.01)
  *A61K 35/12* (2015.01)

(56) References Cited

U.S. PATENT DOCUMENTS 7,854,717 B1 * 12/2010 Lentz .......................... 604/5.01

2008/0159998 A1 * 7/2008 Ichim .......................... 424/93.21

OTHER PUBLICATIONS

Yong Zhao, Honglan Wang, Theodore Mazzone, Identification of stem cells from human umbilical cord blood with embryonic and hematopoietic characteristics, 312 Experimental Cell Research, 2454-2464 (2006).*

* cited by examiner cont.

SEQUENCE LISTING

```
<160> NUMBER OF SEQ ID NOS: 2

<210> SEQ ID NO 1
<211> LENGTH: 1307
<212> TYPE: DNA
<213> ORGANISM: Homo sapiens

<400> SEQUENCE: 1
aagagaaaac tcctccaaaa gcagctctca ctatcagaaa acccaactac agttgtgaac      60
gccttcattt tctgcctgag gtctcagtcc gtcggcccag actgaagtgc agtggcacaa     120
tcatagctcg ctgcagcctc gaccttccag gcttaaacga ttctcccacc tcagcctctc     180
gagttgctgg gaccacaggt cactgtgcat ggcatcatcc tggcccctc tagagctcca      240 atcctccaac cagagccagc tcttccctca aaatgctacg gcctgtgaca atgctccaga     300
agcctgggac ctgctgcaca gagtgctgcc aacatttatc atctccatct gtttcttcgg     360
cctcctaggg aacctttttg tcctgttggt cttcctcctg ccccggcggc aactgaacgt     420
ggcagaaatc tacctggcca acctggcagc ctctgatctg gtgtttgtct tgggcttgcc     480
cttctgggca gagaatatct ggaaccagtt taactggcct ttcggagccc tcctctgccg     540
tgtcatcaac ggggtcatca aggccaattt gttcatcagc atcttcctgg tggtggccat     600
cagccaggac cgctaccgcg tgctggtgca ccctatggcc agccggaggc agcagcggcg     660
gaggcaggcc cgggtcacct gcgtgctcat ctgggttgtg gggggcctct tgagcatccc     720
cacattcctg ctgcgatcca tccaagccgt cccagatctg aacatcaccg cctgcatcct     780
gctcctcccc catgaggcct ggcactttgc aaggattgtg gagttaaata ttctgggttt     840
cctcctacca ctggctgcga tcgtcttctt caactaccac atcctggcct ccctgcgaac     900
```

| | |
|---|---:|
| gcgggaggag gtcagcagga caaggtgcgg gggccgcaag gatagcaaga ccacagcgct | 960 |
| gatcctcacg ctcgtggttg ccttcctggt ctgctgggcc ccttaccact tctttgcctt | 1020 |
| cctggaattc ttattccagg tgcaagcagt ccgaggctgc ttttgggagg acttcattga | 1080 |
| cctgggcctg caattggcca acttctttgc cttcactaac agctccctga atccagtaat | 1140 |
| ttatgtcttt gtgggccggc tcttcaggac caaggtctgg gaactttata acaatgcac | 1200 |
| ccctaaaagt cttgctccaa tatcttcatc ccataggaaa gaaatcttcc aacttttctg | 1260 |
| gcggaattaa aacagcattg aaccaagaaa aaaaaaaaa aaaaaa | 1307 |

```
<210> SEQ ID NO 2
<211> LENGTH: 1638
<212> TYPE: DNA
<213> ORGANISM: Homo sapiens

<400> SEQUENCE: 2
```

| | |
|---|---:|
| atggcgacgg acgcggcgct acgccggctt ctgaggctgc accgcacgga gatcgcggtg | 60 |
| gccgtggaca gcgccttccc actgctgcac gcgctggctg accacgacgt ggtccccgag | 120 |
| gacaagtttc aggagacgct tcatctgaag gaaaaggagg gctgccccca ggccttccac | 180 |
| gccctcctgt cctggctgct gacccaggac tccacagcca tcctggactt ctggagggtg | 240 |
| ctgttcaagg actacaacct ggagcgctat ggccggctgc agcccatcct ggacagcttc | 300 |
| cccaaagatg tggacctcag ccagcccggg aaggggagga agccccggc cgtccccaag | 360 |
| gctttggtac cgccacccag actccccacc aagaggaagg cctcagaaga ggctcgagct | 420 |
| gccgcgccag cagccctgac tccaaggggc accgccagcc caggctctca actgaaggcc | 480 |
| aagcccccca agaagccgga gagcagcgca gagcagcagc gccttccact cgggaacggg | 540 |
| attcagacca tgtcagcttc agtccagaga gctgtgccca tgtcctccgg ggacgtcccg | 600 |
| ggagcccgag gggccgtgga gggatcctc atccagcagg tgtttgagtc aggcggctcc | 660 |
| aagaagtgca tccaggttgg cggggagttc tacactccca gcaagttcga agactccggc | 720 |
| agtgggaaga acaaggcccg cagcagcagt ggcccgaagc ctctggttcg agccaaggga | 780 |
| gcccagggcg ctgccccgg tggaggtgag gctaggctgg gccagcaggg cagcgttccc | 840 |
| gcccctctgg ccctccccag tgaccccag ctccaccaga gaatgagga cgagtgtgcc | 900 |
| gtgtgtcggg acgcggggga gctcatctgc tgtgacggct gccctcgggc cttccacctg | 960 |
| gcctgcctgt cccctccgct ccgggagatc cccagtggga cctggaggtg ctccagctgc | 1020 |
| ctgcaggcaa cagtccagga ggtgcagccc cgggcagagg agccccggcc ccaggagcca | 1080 |
| cccgtggaga ccccgctccc cccggggctt aggtcggcgg gagaggaggt aagaggtcca | 1140 |
| cctggggaac ccctagccgg catggacacg actcttgtct acaagcacct gccggctccg | 1200 |
| ccttctgcag ccccgctgcc agggctggac tcctcggccc tgcaccccct actgtgtgtg | 1260 |
| ggtcctgagg gtcagcagaa cctggctcct ggtgcgcgtt gcggggtgtg cggagatggt | 1320 |
| acggacgtgc tgcggtgtac tcactgcgcc gctgccttcc actggcgctg ccacttccca | 1380 |
| gccggcacct cccggcccgg gacgggcctg cgctgcagat cctgctcagg agacgtgacc | 1440 |
| ccagcccctg tgaggggt gctggccccc agcccgccc gcctggcccc tgggcctgcc | 1500 |
| aaggatgaca ctgccagtca cgagcccgct ctgcacaggg atgacctgga gtcccttctg | 1560 |
| agcgagcaca ccttcgatgg catcctgcag tgggccatcc agagcatggc ccgtccggcg | 1620 |
| gccccctccc cctcctga | 1638 |

STEM CELL IMMUNE MODULATION METHODS OF USE AND APPARATUS

CROSS-REFERENCE TO RELATED APPLICATION

This application claims the benefit of U.S. Provisional Patent Application Ser. No. 61/283,782, filed Dec. 8, 2009, entitled "Stem cell educator and clinical applications" and U.S. Provisional Patent Application Ser. No. 61/283,810, filed Dec. 8, 2009, entitled "Stem cell immune modulation and its molecular mechanisms," the disclosures of which are incorporated by reference herein in their entirety. This application is also a continuation-in-part of U.S. patent application Ser. No. 12/099,054 filed Apr. 7, 2008 entitled Isolate Embryonic-Like Stem Cells Derived from Human Umbilical Cord Blood," likewise incorporated by reference herein in its entirety.

TECHNICAL FIELD

The present invention is related generally to methods and apparatus for the treatment of autoimmune diseases and immune disorder-related diseases.

BACKGROUND OF THE INVENTION

The increasing prevalence of human autoimmune diseases and immune disorder-related diseases, e.g. cardiovascular disease, diabetes, and neuronal degenerative diseases, presents a challenge to find more effective therapies. Stem cell-based therapy, including embryonic and adult stem cells, provides a rational treatment tool for regenerative medicine and has potential to revolutionize modern therapeutics. Because of their high potential for self renewal and pluripotent differentiation capability, embryonic stem (ES) cells have become a very active area of investigation. Ethical concerns, however, have limited their availability and practical usefulness. Leaving aside these ethical concerns, using in vitro fertilization (IVF) and altered nuclear transfer (ANT) to generate ES cells is made problematic by the complexity of required technologies.

Recently, human umbilical cord blood has been used as a source of stem cells to repopulate the hematopoietic system and other organs. Cord blood provides an abundant source for generation of stem cells, including mesenchymal stem cells and monocyte-derived stem cells. Stem cells expressing ES molecular markers have been reported from cord blood after removal of hematopoietic cells (including deletion of all leukocyte common antigen CD45 positive cells). However, the scarcity of this previously-described cell population [in cord blood significantly restricts its practical application.

Several other embryonic-like stem cells derived from adult sources rather than embryonic sources have also been disclosed. For example, U.S. Pat. No. 7,045,148, United States Patent Applications Serial Numbers 2005/0148034, 2005/0118715, 2004/0028660, 2003/0235909, 2002/0160510, 2003/0180269 and International Patent Application Number WO 03/068937 disclose embryonic-like stem cells extracted from the placenta or from the umbilical cord blood. United States Patent Application Serial Number 2006/0078993 discloses embryonic-like stem cells derived from the amniotic membrane of umbilical cord. The stem cells disclosed in these patents or patent applications are of mesenchymal origin which do not express the CD45 marker (CD45$^-$). In another example, United States Patent Application Serial Number 2006/0147426 discloses stem cells derived from human bone marrow. International Application PCT/US06/38524 by Zhao and Mazzone discloses an embryonic-like stem cell isolated from the umbilical cord blood that is suitable for stem cell therapies. Additionally, International Application PCT/US07/22260 by Zhao and Mazzone discloses an embryonic-like stem cell isolated from the peripheral blood that is also suitable for stem cell therapies.

BRIEF SUMMARY OF THE INVENTION

Methods and apparatus are disclosed that utilize stem cells with embryonic-like stem cell characteristics to educate autoreactive immune cells as a mechanism to treat autoimmune diseases.

In one aspect of the invention, bioreactors are disclosed for modulating lymphocytes and suppressing autoreactive T cells, having a chamber having at least one positively charged and/or hydrophobic substrate surface, a population of stem cells attached to the substrate surface, an inlet conduit for introducing lymphocytes into the chamber, and an outlet conduit for extracting treated lymphocytes following co-culturing with the stem cells.

The bioreactor's substrate surface can be formed as one or more sheet layers. Alternatively, the substrate surface can be formed by a plurality of microcarriers. In yet another embodiment, the he substrate surface can be a permeable membrane layer.

In some embodiments, the substrate surface comprises hydrophobic polymer, such as polystyrene to which stem cells readily attach. The stem cells can exhibit a confluence of at least 50%, 60%, 70%, 80%, 90% or even 95% on the substrate surface. The bioreactor preferably houses a population of at least $10^6$ stem cells within the chamber. In some instances, the stem cells are present within the chamber in a ratio to the lymphocytes of at least 1:10.

The bioreactor's chamber can be constructed to permit cell-to-cell contact between the stem cells and the lymphocytes or to prevent such cell-to-cell contact e.g., to avoid entrainment of stem cells when the treated lymphocytes are removed from the chamber. Moreover, the stem cells can be cultured onto multiple substrate surface layers within the chamber.

The stem cells can be obtained from umbilical cord blood or peripheral blood. The stem cells can be allogenic to the lymphocytes or autologous to the lymphocytes.

In another aspect of the invention, systems for inhibiting an autoimmune disorder are disclosed having a fluid conduit for extracting blood from a subject; an apheresis apparatus for separating lymphocytes from the extracted blood; and a bioreactor having a chamber with at least one positively charged and/or hydrophobic substrate surface such that a population of stem cells can be attached to the substrate surface, an inlet conduit for introducing lymphocytes into the chamber, and an outlet conduit for extracting treated lymphocytes following co-culturing with the stem cells; and a fluid conduit for returning treated lymphocytes to the subject. The bioreactor can have all or any of the above-described elements, features or functions.

In another aspect of the invention, methods of inhibiting an autoimmune disorder due to autoreactive T cells are disclosed involving the steps of extracting blood from a subject in need of treatment, isolating lymphocytes from the extracted blood, exposing the lymphocytes to stem cells such that regulatory T (Treg) cells are activated to suppress autoreactive T cells, and returning at least a portion of the treated lymphocytes to the subject. For example, the method can be practiced where the autoimmune disorder is diabetes.

The step of exposing the lymphocytes to stem cells can further include: culturing the stem cells in a reactor, e.g., by growing the stem cells to confluence on a substrate surface having a net positive charge, and introducing the subject's lymphocytes into the reactor.

The method can be practiced with stem cells that are allogenic or autologous to the subject's lymphocytes. The stem cells can be obtained from umbilical cord blood or from peripheral blood, e.g., autologous stem cells obtained from a subject's own peripheral blood.

The step of culturing the stem cells in the bioreactor can further include collecting peripheral blood comprising peripheral blood mononuclear cells (PBMCs); culturing the PBMCs, such that the PBMCs revert to embryonic-like stem cells; isolating the embryonic-like stem cells; and attaching the embryonic-like stem cells to a surface of the reactor.

The method can involve modulating Treg cells by expression of a programmed death ligand 1 (PD-L1) by the stem cells and/or wherein the Treg cells are activated by release of nitric oxide (NO) by the stem cells. The method can involve activation of the Treg cells by cell-to-cell contact with the stem cells and/or by soluble factors secreted by the stem cells within the reactor. The method of activating regulatory T (Treg) cells can further involve exposing the Treg cells to stem cells expressing carboxypeptidase M (CPM) or to a stem cells expressing brady kinin B1 receptor or by exposing the Treg cells to stem cells expressing autoimmune regulator (AIRE) protein.

The modulated/activated Treg cells can be characterized by expression of at least one of the CD4, CD25, CD62L and CD69 markers and preferably all of these markers.

In one embodiment the steps of extracting blood and returning the treated lymphocytes to the subject can be performed in a continuous manner. For example, the subject's blood can be continuously processed for a duration sufficient to extract at least 1 liter of the subject's blood.

In another aspect, the invention discloses a method of harvesting embryonic-like stem cells from a subject comprising extracting stem cells from a source comprising embryonic-like stem cells; culturing the stem cells in growth medium, such that the stem cells revert to embryonic-like stem cells; and isolating the embryonic-like stem cells. In some embodiments, the growth medium can comprises media with and without serum. The cells do not require feeder cell layers to grow in vitro and does not form teratomas when grown in vivo. Culturing can further include seeding the stem cells on a surface with a hydrophobic surface, such as polystyrene or other suitable plastic materials and glass.

In some embodiments, the embryonic-like stem cells express at least one of Octamer-binding transcription factor 4 (Oct-4), Nanog homeobox (Nanog), SRY (sex determining region Y)-box 2 (Sox-2), CD9, CD45, a carboxypeptidase M (CPM), a bradykinin B1 receptor (B1R) and a programmed death ligand 1 (PD-L1). In another embodiment, the embryonic-like stem cells expresses inducible nitric oxide synthase (iNOS). In yet another embodiment, the embryonic-like stem cells expresses autoimmune regulator (AIRE).

In another aspect, the invention discloses a method of educating and modulating lymphocytes or lymphocyte function in a subject in need thereof, comprising coculturing a first population of embryonic-like stem cells with a second population of cells comprising lymphocytes, administering at least the treated second cell population after coculturing to a subject. The lymphocytes (including T lymphocytes and B lymphocytes) can be allogeneic lymphocytes, or autologous lymphocytes from human peripheral blood. Culturing the lymphocytes with the embryonic-like stem cells modulates the lymphocytes. For example, the modulation can include mediating expression of self-antigens. In another embodiment, the embryonic-like stem cells modulate CD4+, CD62L+ T lymphocytes. The method can include up-regulating nitric oxide (NO) production. In yet another embodiment, method can increase expression of autoimmune regulator (AIRE). In some embodiments, the method can be used to treat, ameliorate the symptoms or delay onset of type I diabetes.

In yet another aspect, the invention discloses a method of treating diabetes in a mammalian subject in need thereof, comprising removing at least one autoimmune lymphocyte from the subject; co-culturing embryonic-like stem cells with the lymphocyte; and administering the lymphocyte back to the subject to treat diabetes. In one embodiment, the lymphocytes are removed from peripheral blood of the subject. The subject may under cytopheresis to obtain the lymphocytes. In another embodiment, the lymphocytes are CD4+, CD62L+ T lymphocytes. The administering step can be through any suitable method, for example, intravenous or intraarterial injection. The cells can be administered in an amount of from about $1 \times 10^4$-$1 \times 10^{13}$ cells per subject. The method can be used to treat or ameliorate the symptoms of insulin-dependent diabetes. In some embodiments, the lymphocytes are obtained from peripheral blood through cytopheresis.

In another aspect, the invention discloses an apparatus for co-culturing the stem cells with a second population of cells. The apparatus can be multi-tiered for a plurality of layers of stem cells with flow through holes for cells and/or liquid to pass from one layer to another. In one embodiment, the apparatus has surface with a hydrophobic surface, such as polystyrene or other suitable plastic materials and glass. In another embodiment, the stem cells adhere to the surface of the apparatus. The apparatus can further have an input and an output. A second population of cells flows into the apparatus through the input. The second population can be co-cultured with the stem cells then flow out of the output of the apparatus. The apparatus can also be a closed system, with direct connections to a continuous inflow providing the second population of cells and a continuous outflow removing the co-cultured cells. The continuous inflow can be provided from a source such as an apheresis machine. In another embodiment, the continuous outflow can be removed by a source such as an apheresis machine.

The apparatus can further comprise a membrane separator between the stem cells and the second population of cells. The membrane can be a porous membrane. The porous membrane has sufficiently small pores to prevent stem cells from passing through the membrane. In another embodiment, the porous membrane has sufficiently large pores to allow passage of factors from one side of the membrane to the other. In one embodiment, the stem cells are adhered to one surface of the porous membrane. In another embodiment, the pores are no greater than about half the size of an average stem cell.

BRIEF DESCRIPTION OF THE DRAWINGS

FIG. 8A show intra-cellular cytokine staining;

FIG. 8B shows intra-cellular Foxp3 staining;

FIG. 8C shows cell proliferation assay. T1D patient-derived GAD-specific CD4+ T cell clone was co-cultured for 3 days with CB-SC in the presence of antigen-presenting cells (APC) and specific GAD peptide or non-specific control proinsulin peptide;

DETAILED DESCRIPTION OF THE INVENTION

Figure 1:
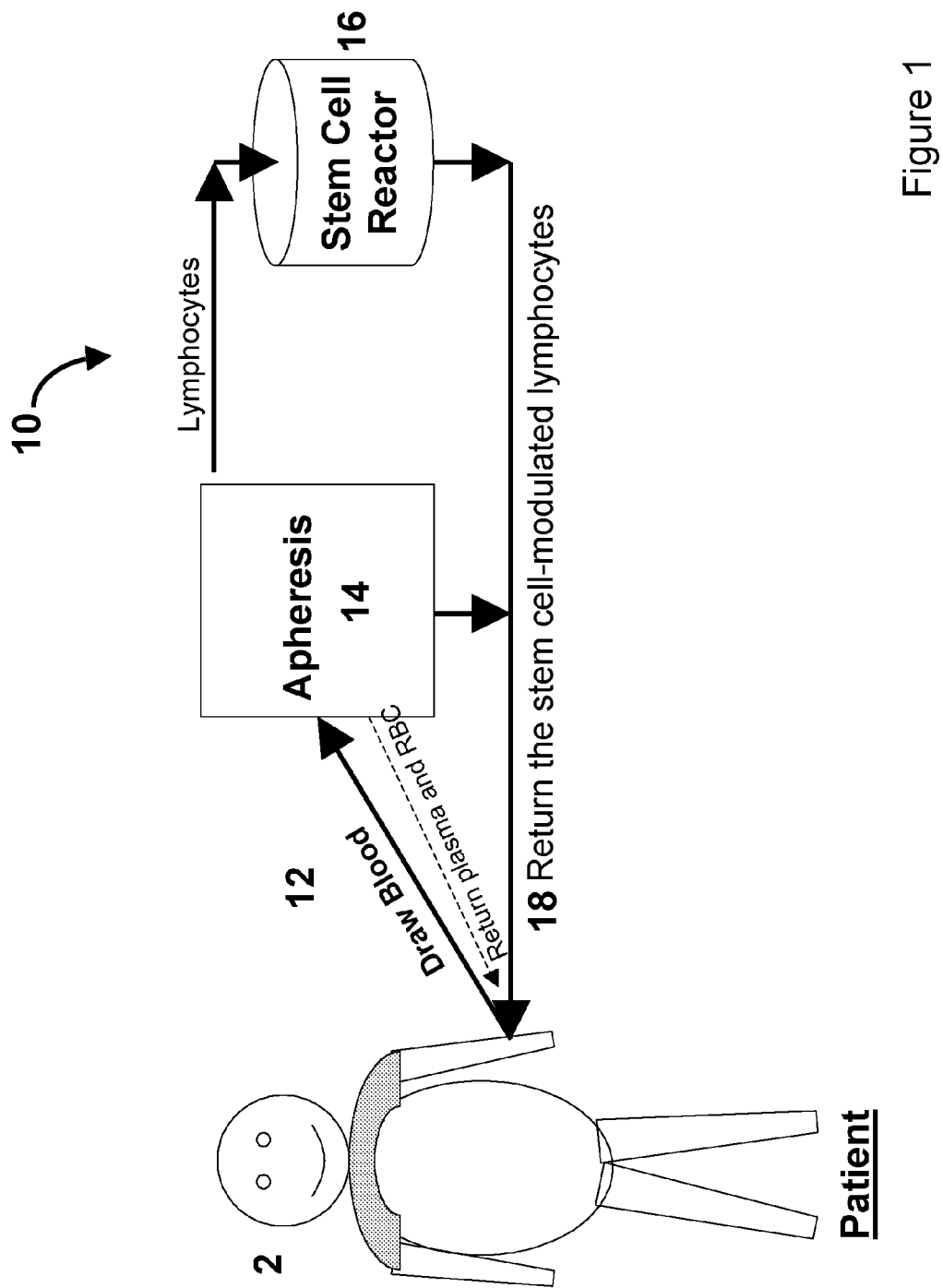
FIG. 1 is a schematic illustration of a system according to the invention for treatment of autoimmune disorders, using a Blood Cell Separator MCS+ with a single needle procedure.

The present invention discloses method and apparatus for a novel use of stem cells. These stem cells can be of cord blood or peripheral blood (and not mesenchymal) origin. These cells can be isolated and expanded using simple technology. A particularly useful aspect of the invention is that these cells can be isolated from the peripheral blood of an individual, particularly an adult individual, for autologous stem cell therapies, or the cells can be isolated from another individual for non-autologous stem cell therapies. The present invention also discloses the use of stem cells in modulating the function of mononuclear cells, such as T lymphocytes, B lymphocytes, monocytes, dendritic cells (DC) and granulocytes.

In a preferred embodiment, the stem cells have characteristics including, but not limited to, stem cell markers Oct-4, Nanog, and Sox-2, together with other embryonic stem (ES) cell-related genes, e.g., Zinc finger and SCAN domain containing 10 (ZNF206, also named ZSCAN10), Zic family member 3 heterotaxy 1 (ZIC3), Zic family member 2 (ZIC2), Growth associated protein 43 (GAP43), PR domain containing 14 (PRDM14), Protein tyrosine phosphatase, receptor-type, Z polypeptide 1 (PTPRZ1), Podocalyxin-like (PODXL), Polyhomeotic homolog 1 (PHC1), Zinc finger protein 589 (ZNF589) a carboxypeptidase M (CPM), a bradykinin B1 receptor (B1R) (SEQ ID NO:1) and a programmed death ligand 1 (PD-L1). In another embodiment, the embryonic-like stem cells expresses inducible nitric oxide synthase (iNOS). In yet another embodiment, the embryonic-like stem cells expresses autoimmune regulator (AIRE) (SEQ ID NO:2). The sequences for Oct-4, Nanog, and Sox-2 can be found under GenBank Accession Nos. NM_002701, Z11898 and Q01860; GenBank Accession Nos. NM_024865 and NP_079141; and GenBank Accession Nos. Z31560 and CAA83435, respectively.

In another embodiment, the stem cells can also have hemotopoietic characteristics characterized by expression of leukocyte common antigen CD45. In a further embodiment, the stem cells do not express CD3, CD20 (B-lymphocyte cell-surface antigen B1, Accession No. M27394), CD11c (integrin, alpha X, Accession No. NM_000887), CD11b/Mac-1 (complement component 3 receptor 3 subunit, Accession No. NM_000632) and CD14 (Accession Nos. NM_001040021 and P08571) markers. In still another embodiment, the stem cells do not express the CD34 marker (Hematopoietic progenitor cell antigen CD34, Accession No. P28906).

The present invention also discloses the use of stem cells to prevent or delay onset of and/or reverse or treat autoimmune disorders and diseases, such as diabetes (including type 1, type 1.5 and type 2). As shown in the Examples, after co-culturing with stem cells, various populations of T lymphocytes can be isolated and administered to a subject to prevent or delay onset of and/or reverse or treat autoimmune disorders and diseases, such as diabetes. For example, T cells that are positive for the CD62L marker (a marker for memory lymphocytes) can be isolated. CD4+CD25+CD62L+CD69+ T cells can significantly delay diabetes onset in a subject at risk. For example, administration of CD4+CD25+CD62L+CD69+ T cells was shown to modulate the initiation stage of autoimmune responses of diabetic NOD mice and significantly delayed diabetes onset. Following administration of either CD4+CD25+CD62L+CD69+ T cells, the autoimmune disorder or disease, such as diabetes, can be reversed to achieve euglycemia.

The present invention further discloses a method and apparatus for stem cell-based therapy comprising the embryonic-like stem cells of the present invention. In one embodiment, the stem cells are used for treating an autoimmune disease and immune disorder-related diseases, such as diabetes, in a mammalian subject.

In yet another embodiment, the present invention discloses a method for immunoregulation of at least one autoimmune lymphocyte. The method comprises providing a sample of adult human peripheral blood; extracting lymphocytes from the sample; co-culturing the lymphocytes with the stem cells; harvesting the lymphocytes cells from the co-culture and administering the lymphocytes back into the subject. The stem cells can be attached to a surface of a bioreactor. Furthermore, the stem cells do not require a cell feeder layer. The present invention is suitable for stem cell-based co-culture therapies, autologous and non-autologous cell therapies.

Regulatory T cells (Tregs) play a crucial role in maintaining homeostasis and self-tolerance through their inhibitory impact on autoreactive effector T cells, such as releasing immunosuppressive cytokines interleukin-10 (IL-10) and/or transforming growth factor-beta1 (TGF-beta1). Increasing evidence demonstrates that abnormalities of Tregs, either in cell number or in function, are associated with initiation and progression of autoimmune diseases, such as diabetes. The manipulation of Tregs for treatment of autoimmune diseases is novel approach. A limited number of studies have focused on restoration of impaired Treg function to confer protection against autoimmune diabetes but not modulation of Treg function. Stem cells, as disclosed herein, can correct functional defects of Tregs, leading to reversal of overt autoimmune diseases, such as diabetes.

In one aspect, the stem cells of the present invention can be co-cultured with T lymphocytes, thereby enhancing the production of various populations of T cells that can prevent, delay, treat, and/or reduce diabetes. In some embodiments, co-cultured lymphocytes can be administered to a subject to delay onset, reduce or ameliorate an autoimmune disorder, such as diabetes. In other embodiments, the co-cultured lymphocytes can include at least one CD4+CD25+CD62L+ CD69+ T cell. In yet other embodiments, T cells that are positive for CD62L and positive for at least one of CD69 or CD4 can be administered to reduce at least one symptom of an autoimmune disorder, such as diabetes, or ameliorate the disorder in a subject. For example, co-cultured lymphocytes can be administered to a subject, wherein glucose levels in said subject are reduced to levels with normal ranges for said subject. In some embodiments, the co cultured lymphocytes can be expanded in vitro by using lymphocyte growth factors. Non-limiting examples of growth factors that can be used to expand the population of co-cultured lymphocytes and/or specific subpopulations of co-cultured lymphocytes (such as, for example, CD4+CD25+CD62L+CD69+ T cells).

I. DEFINITIONS

The terms used in this invention are, in general, expected to adhere to standard definitions generally accepted by those having ordinary skill in the art of molecular biology. A few exceptions, as listed below, have been further defined within the scope of the present invention.

As used herein, the terms "embryonic stem cell" refers to a stem cell that is derived from the inner cell mass of a blastocyst (e.g., a 4- to 7-day-old human embryo) and that is pluripotent. The terms "embryonic-like stem cell", "stem cell," "cord blood-stem cell (CB-SC)", and "cord blood derived insulin-producing cells (CB-IPC)" "peripheral blood-stem cell (PB-SC)", and "peripheral blood derived insulin-producing cells (PB-IPC)" are used interchangeably herein to refer to a stem cell that is not derived from the inner cell mass of a blastocyst. An embryonic-like stem cell is pluripotent. The embryonic-like stem cells display at least a subset of characteristics of embryonic stem cells (ES) and hematopoietic cells. The term "stem cell" refers to a master cell that can reproduce indefinitely to form the specialized cells of tissues and organs. A stem cell is a developmentally pluripotent or multipotent cell. A stem cell can divide to produce two daughter stem cells, or one daughter stem cell and one progenitor ("transit") cell, which then proliferates into the tissue's mature, fully formed cells. The "stem cell" used herein includes "progenitor cells" unless otherwise noted.

As used herein, the term "pluripotential", "pluripotential for differentiation" or "pluripotent" refers that the cell is positive for one or more of the pluripotent markers such as but are not limited to Oct-4, Nanog, and Sox-2 and the cell has the potential to differentiate to at least a subset of the mammalian body's approximately 260 cell types upon appropriate stimulations such as by the appropriate growth factors.

As used herein, the term "totipotent cell" refers to a cell that is able to form a complete embryo (e.g., a blastocyst).

The term "subject" refers to any living organism in which an immune response is elicited. The term refers to a living animal or human in need of treatment for, or susceptible to, a condition involving an unwanted or undesirable microorganism, e.g., a particular treatment for having an unwanted pathogenic cell as defined below. The term subject includes, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered. In preferred embodiments, the subject is a mammal, including humans and non-human mammals. In the most preferred embodiment, the subject is a human.

The term "undifferentiated" as used herein refers to pluripotent embryonic stem cells which have not developed a characteristic of a more specialized cell. As will be recognized by one of skill in the art, the terms "undifferentiated" and "differentiated" are relative with respect to each other. A stem cell which is "differentiated" has a characteristic of a more specialized cell. Differentiated and undifferentiated cells are distinguished from each other by several well-established criteria, including morphological characteristics such as relative size and shape, ratio of nuclear volume to cytoplasmic volume; and expression characteristics such as detectable presence of known markers of differentiation. A marker of differentiation indicating that cells are differentiated or undifferentiated includes a protein, carbohydrate, lipid, nucleic acid, functional characteristic and/or morphological characteristic which is specific to a differentiated cell.

As used herein, the term "substantially homogeneous" when applied to cells, refers to a population of cells, wherein at least about 70%, and preferably about 80%, more preferably 90% of the cells in the population are of the same cell type. Examples of cell types include, but are not limited to, embryonic-like stem cells, beta cell-like insulin-producing cells, neuronal cells, cardiomyocyte cells, megakaryocyte cells, endothelial cells, epithelial cells, red blood cells, lymphocytes, monocytes, macrophages, granulocytes, hepatocytes, nephrogenic cells, adipogenic cells, osteoblast cells, osteoclastic cells, alveolar cells, cardiac cells, intestinal cells, renal cells, retinal cells, and the like. In some embodiments, the term "substantially homogeneous" describes a population of cells wherein at least about 70%, and preferably about 80%, more preferably 90% of the cells in the population are undifferentiated. In a further embodiment a substantially homogeneous population of cells is one in which more than 95% of the cells are undifferentiated. In another embodiment, a substantially homogeneous population of cells is one in which more than 99% of the cells are undifferentiated. A population of cells can be assayed for one or more markers of differentiation to determine whether the population of cells is substantially homogeneous.

The production and/or maintenance of a substantially homogeneous population of embryonic-like stem cells and/or a differentiated cell type may be measured by assessing the proportion of cells for particular markers of undifferentiated cells and/or differentiated cells. For example, relative ratios of transcription products for markers of undifferentiated cells such as Oct4, neuroprogenitor markers such as nestin and Ngn-3, and markers of mature neuron markers such as β-tubulin and TPH2 is assessed by quantitative RT-PCR. Also, production and localization of markers of undifferentiated cells can be assessed by immunocytochemistry.

Markers of undifferentiated stem cells and differentiated cells are assayed by any of various methods such as antibody-based detection techniques using an antibody specific for a particular marker. Antibody-based techniques include immunofluorescence and immunoblotting. Further assays include assays for detection of mRNAs encoding a particular marker. Such assays include polymerase chain reaction, blot hybridization (also known as Northern blots) and in situ hybridization. Details of these and other such assays are described herein and in standard references including J. Sambrook and D. W. Russell, Molecular Cloning: A Laboratory Manual, Cold Spring Harbor Laboratory Press; 3rd ed., 2001; F. M. Ausubel, Ed., Short Protocols in Molecular Biology, Current Protocols; 5th ed., 2002; and E. Harlow and D. Lane, Antibodies: A Laboratory Manual, Cold Spring Harbor Laboratory Press, 1988.

As used herein, the terms "lymphocytes" and "leukocyte" are used interchangeably and refer generally to hematopoetic, mononuclear cells, that include but are not limited to, white blood cells, T cells and B cells, T lymphocytes, effector T cell, Treg cells, immature T cells, B lymphocytes, immature B cells, mature B cells, hematopoietic antigen presenting cells, memory B cells.

As used herein, the term "culture medium" refers generally to any substance or preparation used for the cultivation of living cells. A "cell culture" refers to a growth of cells in vitro; although the cells proliferate they do not organize into tissue per se.

As used herein, the terms "treat," "treating," "treatment," and the like refer to reducing or ameliorating a disorder and/or symptoms associated therewith. Although not precluded, treating a disorder or condition does not require that the disorder, condition or symptoms associated therewith be completely eliminated. As used herein, the terms "prevent," "preventing," "prevention," and the like include "prophylactic treatment" which refers to reducing the probability of developing a disorder or condition in a subject, who does not have, but is at risk of or susceptible to developing a disorder or condition.

The term "administration" or "administering" is used throughout the specification to describe the process by which embryonic-like stem cells according to the present invention are delivered to a subject. The embryonic-like stem cells can be administered a number of ways including parenteral (such term referring to intravenous and intraarterial as well as other appropriate parenteral routes), intrathecal, intraventricular, intraparenchymal (including into the spinal cord, brainstem or motor cortex), intracisternal, intracranial, intrastriatal, and intranigral, among others which term allows the cells to migrate to the site where needed. The compositions according to the present invention can be used without treatment with an inducer ("untreated", i.e., without further treatment in order to promote differentiation of cells within the stem cell sample) or after treatment ("treated") with an inducer or other agent which causes the embryonic-like stem cells to differentiate into cells exhibiting a favorable phenotype. Administration will often depend upon the disease or condition treated and can preferably be via a parenteral route, for example, intravenously, by administration into the cerebral spinal fluid or by direct administration into the affected tissue in the brain or other body site. For example, in the case of diabetes, the preferred route of administration will into the pancreas or it can be by an intravenous route to allow transmigration through the circulatory system and "homing" to the affected site.

The terms "autoimmune disorder" and "autoimmune disease" are used throughout the specification synonymously to describe diseases having autoimmune manifestations, such as Addison's disease, autoimmune hemolytic anemia, autoimmune thyroiditis, Crohn's disease, diabetes (Type I), Graves' disease, Guillain-Barre syndrome, systemic lupus erythematosus (SLE), lupus nephritis, multiple sclerosis, myasthenia gravis, psoriasis, primary biliary cirrhosis, rheumatoid arthritis and uveitis, asthma, atherosclerosis, Type I diabetes, psoriasis, and various allergies.

The term "immune disorder-related disease" is used throughout the specification synonymously to describe diseases having immune disorders contributing the pathogenesis of diseases, such as type II diabetes, obese, cardiovascular diseases, high blood pressure, hyperlipidemia, chronic kidney disease, a primary glomerulonephritis; purpura nephritis, lupus nephritis, diabetic nephropathy, diabetic foot, and diabetic eyes.

The terms "grafting" and "transplanting" and "graft" and "transplantation" are used throughout the specification synonymously to describe the process by which embryonic-like stem cells or other cells according to the present invention are delivered to the site where the cells are intended to exhibit a favorable effect, such as treating autoimmune diseases and treating diabetes. The embryonic-like stem cells or other cells for use in the present invention can also be delivered in a remote area of the body by any mode of administration as described above, relying on cellular migration to the appropriate area in the body to effect transplantation.

The term "essentially" is used to describe a population of cells or a method which is at least 90% effective, more preferably at least about 95% effective and even more preferably at least 98% effective. Thus, a method which "essentially" eliminates a given cell population, eliminates at least about 90% of the targeted cell population, most preferably at least about 98% of the cell population. Embryonic-like stem cells according, in certain embodiments, are essentially free of hematopoietic cells (i.e., negative for hematopoietic stem cell marker CD34), essentially free of lymphocyte (i.e., negative for lymphocyte markers CD3, CD20, and CD90), essentially free of monocyte/macrophage antigens CD11b/Mac-1 and CD14, essentially free of dendritic cell antigen CD11c, and essentially free of mesenchymal (CD45$^-$) cells.

The term "non-tumorigenic" refers to the fact that the cells do not give rise to a neoplasm or tumor. The embryonic-like stem cells for use in the present invention are generally free from neoplasia and cancer.

II. METHODS OF STEM CELL ISOLATION

The present invention discloses a use of a population of stem cells isolated from embryonic cord blood or peripheral blood. They are designated herein as cord blood-stem cells (CB-SC) or peripheral blood-stem cells (PB-SC). As used herein, the terms "umbilical cord blood" and "cord blood" are interchangeable.

According to the methods of the invention, stem cells represent the attached population of cells during co-culturing with a population of lymphocytes. The lymphocytes from adult human peripheral blood. The lymphocytes can be also be, but are not limited to, umbilical cord blood, bone marrow cells, splenic cells, thymic cells, lymphnodes, adipocyte tissues and liver cells. The lymphocytes can be co-cultured in very basic cell culture medium with a low percentage of serum (e.g., 7% fetal bovine serum), serum-free cell culture medium and without cell feeders. The attached stem cell population can be attached to a positively charged surface. The surface can also be a hydrophobic surface, for example, such as polystyrene and glass.

What is meant by "isolated" in the present invention is that the stem cells or lymphocytes are separated from other cells, such as the red blood cells and other unattached mononuclear cells, found in the umbilical cord blood or peripheral blood through one or more isolation methods such as, but are not limited to, mechanical separation or selective culturing. Other cell types that may be present in the second population of cells, may be removed during the co-culturing process or harvest process. In a preferred embodiment, the second population is made up of greater than 50% mononuclear cells. In yet another preferred embodiment, the second population is made up of greater than 75% mononuclear cells. In a further preferred embodiment, the second population is made up of greater than 90% mononuclear cells. In another embodiment, the second population of cells is at least 50% mononuclear cells from adult human peripheral blood after the removal of the red blood cells, bone marrow cells, splenic cells, thymic cells, lymphnodes, adipocyte tissues and liver cells.

III. STEM CELL CHARACTERIZATION

One of the key characteristics for a stem cell to be suitable for stem cell-based therapy is its capability for proliferation. As used herein, the term "capability for proliferation" refers that the cell expresses one or more self-renewal markers such as but are not limited to Nanog and the cell can proliferate. Preferably, the cell can proliferate indefinitely. What is meant by "proliferate" as used in the present disclosure is that the cell can grow and multiply in numbers when the cell is cultured. The terms "proliferate" and "expand" are used interchangeably herein.

Not to be bound by any specific theory, the low immunogenicity of the stem cells can contribute to the ability of the stem cells to regulate immune cells, such as T-lymphocytes. Following co-culture of immune cells with the stem cells, production of inflammatory cytokines produced by the immune cells can be reduced, such as by at least 2-3 fold, and the production of other cytokines may be increased, such as TGF-$\beta$1 is increased by 2-3 fold. Examples of inflammatory cytokines that can be reduced by co-culture with stem cells include TNF-$\alpha$, IL-$\beta$, IL-$\gamma$, IL-15, IL-17, IL-18, IL1$\beta$, IL-21, IL22, IL-23, IL-4, IL-5, and IL-6. Stem cells, when cocultured with immune cells can decrease the percentage of stimulated immune cells, such as CD8$^+$ T cells and IL-2-stimulated CD4$^+$CD25$^+$ regulatory T cells, along with normalization of other immune cells, such as the CD4/CD8 ratio. CD69 molecule, a negative regulator on activated T lymphocytes, can also be increased on immune cells, such as CD4$^+$ and CD8$^+$ T lymphocytes, after coculture with stem cells. In addition, stem cells can inhibit the proliferation of stimulated immune cells, such as IL-2- and/or PHA-stimulated lymphocytes.

Cell-to-cell contract between the stem cells and the lymphocytes may mediate the inhibitory effect. Direct interaction between the stem cells and lymphocytes through cell surface receptors on the stem cell and/or on the lymphocytes. Such receptors can include, but are not limited to, carboxypeptidase M (CPM), bradykinin B1 receptor (B1R) and programmed death ligand 1 (PD-L1).

Soluble factors secreted by the stem cells, such as nitric oxide (NO), may also mediate this inhibitory effect, as demonstrated by blocking with a powerful nitric oxide synthase inhibitor (N-omega-nitro-L-arginine, L-NNA). Furthermore, mechanistic studies demonstrated that CB-SC-produced nitric oxide (NO) contributes to the modulation of CB-SC on regulatory T lymphocytes. The epigenetic regulation on DNA methyltransferase (DNMT) activity of lymphocytes by CB-SC-derived NO can be significantly blocked by presence of a specific inducible nitric oxide synthase (iNOS) inhibitor 1400 W.

IV. METHODS OF TREATMENT

Diabetes is a dominant health problem. Deficit of insulin-producing cells is the crucial issue for both type 1 and type 2 diabetes. Stem cell-derived insulin-producing cells may provide a rational tool for treatment. The key to success for this therapy is the necessity to identify cells that are easy to access, select, culture, expand, and differentiate, without any ethical issues and immune rejection. Both embryonic and adult stem cells can serve as potential sources for clinical therapeutics. However, immune system will recognize and attack foreign cells due to the immune surveillance of human body, even the application of allogeneic embryonic stem cells. Therefore, application of autologous stem cells is a potentially attractive strategy. Increasing evidence shows that human bone marrow and peripheral blood have provided valuable sources for generation of autologous stem cells, including $CD34^+$ hematopoietic stem cells, mesenchymal stem cells, and monocyte-derived stem cells.

The present invention discloses methods for preventing or treating an autoimmune disease in a mammalian subject. The autoimmune disorder can be any one of Addison's disease, autoimmune hemolytic anemia, autoimmune thyroiditis, Crohn's disease, diabetes (Type I), Graves' disease, Guillain-Barre syndrome, systemic lupus erythematosus (SLE), lupus nephritis, multiple sclerosis, myasthenia gravis, psoriasis, primary biliary cirrhosis, rheumatoid arthritis and uveitis, asthma, atherosclerosis, Type I diabetes, Type II diabetes, psoriasis, and various allergies. An example of the autoimmune disease is type 1 diabetes. In an embodiment, mononuclear cells, such as lymphocytes, are harvested from a subject. The mononuclear cells can also be, but are not limited to, bone marrow cells, splenic cells, thymic cells, lymph-nodes, adipocyte tissues and liver cells.

For clinical applications, mononuclear cells may be obtained from the peripheral blood of the subject. The mononuclear cells can also be treated with stem cells, disclosed above, by co-culturing the mononuclear cells with the stem cells to obtain a plurality of stem cell-treated mononuclear cells. During the co-culturing, the stem cells interact directly with the mononuclear cells to modulate their function. Modulated function can be assessed by, but is not limited to, altered expression (increased or decreased) of cell surface expression of markers for quiescence or activation and altered expression (increased or decreased) expression of genes associated with quiescence or activation or cell death. The mononuclear cells are modulated by a decrease in their autoimmunity to self-antigens. After co-culturing, the stem cell-treated mononuclear cells can be harvested. The stem cell-treated mononuclear cells can be administered back to a subject to prevent or treat the autoimmune disease. Preferably, the stem cell-treated mononuclear cells are harvested from the co-culture before administering to the subject. In another embodiment, the stem cell-treated mononuclear cells are harvested from the co-culture simultaneously as they are administered to the subject.

In one aspect, the method is disclosed for preventing or treating an autoimmune disease in a mammalian subject includes a continuous, closed system of removing mononuclear cells from peripheral blood of a subject that contains at least one mononuclear cell, co-culturing the mononuclear cells with stem cells whereby at least one lymphocyte is co-cultured with the stem cells, harvesting the co-cultured mononuclear cells that contain at least one stem cell-treated lymphocyte and administering the co-cultured mononuclear cells that contain at least one stem cell-treated lymphocyte back to the subject. The mononuclear cells can be, but are not limited to, lymphocytes, T lymphocytes, CD4+CD25+ CD62L+CD69+ T lymphocytes, B cells, effector T cell, Treg cells, immature T cells, B lymphocytes, immature B cells, mature B cells, memory B cells, granulocytes, monocytes, dendritic cells, and other antigen presenting cells.

The continuous, closed system can utilize an apheresis technique of obtaining peripheral blood from a subject and separating mononuclear cells and lymphocytes from the peripheral blood of the subject. The mononuclear cells would contain at least one lymphocyte. The subject's peripheral blood can be removed, mononuclear cells separated from the plasma and red blood cells in the peripheral blood, the mononuclear cells can then be transferred to an apparatus for co-culturing with stem cells while the plasma and red blood cells are returned to the subject. The mononuclear cells can be co-cultured with the stem cells by moving a solution containing the mononuclear cells over the stem cells. The mononuclear cells be removed from the co-culture and returned to the subject by gravity or pumping.

In yet another embodiment, the present invention discloses a method for immunoregulating at least one lymphocyte. The method comprises providing a sample of adult human peripheral blood; removing red cells from the sample to obtain mononuclear cells; co-culturing the mononuclear cells with the stem cells; harvesting the mononuclear cells from the co-culture and administering back into the subject. The present invention is suitable for stem cell-based co-culture therapies, autologous and non-autologous cell therapies.

The co-culturing of stem cells with mononuclear cells and/or lymphocytes can lead to activation of the mononuclear cells and/or lymphocytes. Activation is a morphological and functional alterations of the mononuclear cells and/or lymphocytes that may induce synthesis of specific genes related to cell activation such as, but not limited to CD69, CD 100, lymphocyte proliferation potentiation factors, thymocyte-activating factor, CD223 etc. Activation may also induce the mononuclear cells and/or lymphocytes to enter the cell cycle. Activation may also induce the mononuclear cells and/or lymphocytes to proliferate.

In another aspect of the invention, the stem cells are grown to at least 40%, 50%, 60%, 70%, 80%, 85%, 90% or 95% confluence prior to co-culturing with the mononuclear cells and/or lymphocytes. In one embodiment, the stem cells can be co-cultured with the mononuclear cells and/or lymphocytes at a ratio of at least 1:2. In one embodiment, the stem cells can be co-cultured with the mononuclear cells and/or lymphocytes at a ratio of at least 1:5. In one embodiment, the stem cells can be co-cultured with the mononuclear cells and/or lymphocytes at a ratio of at least 1:10. In one embodiment, the stem cells can be co-cultured with the mononuclear cells and/or lymphocytes at a ratio of at least 1:20. In one embodiment, the stem cells can be co-cultured with the mononuclear cells and/or lymphocytes at a ratio of at least 1:50. In one embodiment, the stem cells can be co-cultured with the mononuclear cells and/or lymphocytes at a ratio of at least 1:100.

V. APPARATUS

FIG. 1 illustrates a system 10 according to the invention for treatment of autoimmune disorders having fluid conduit 12 for extracting blood from a subject 2, together with an apheresis apparatus 14, a stem cell reactor 16 and a fluid return conduit 18. In use, blood is extracted from the subject via the fluid conduit 12, e.g. with a hemodynamic pump and processed by an apheresis apparatus 14 to separate lymphocytes from the blood. The blood can be returned to the patient via fluid return conduit 18. The separated lymphocytes are delivered to a stem cell reactor ("stem cell educator") 16 where portions of the lymphocyte population are modified by interactions with stem cells within reactor 16. In one preferred embodiment, the stem cells activate Treg cells, which can be retrieved from the reactor 16 and returned to the subject, e.g., via fluid return conduit 18.

Figure 2:
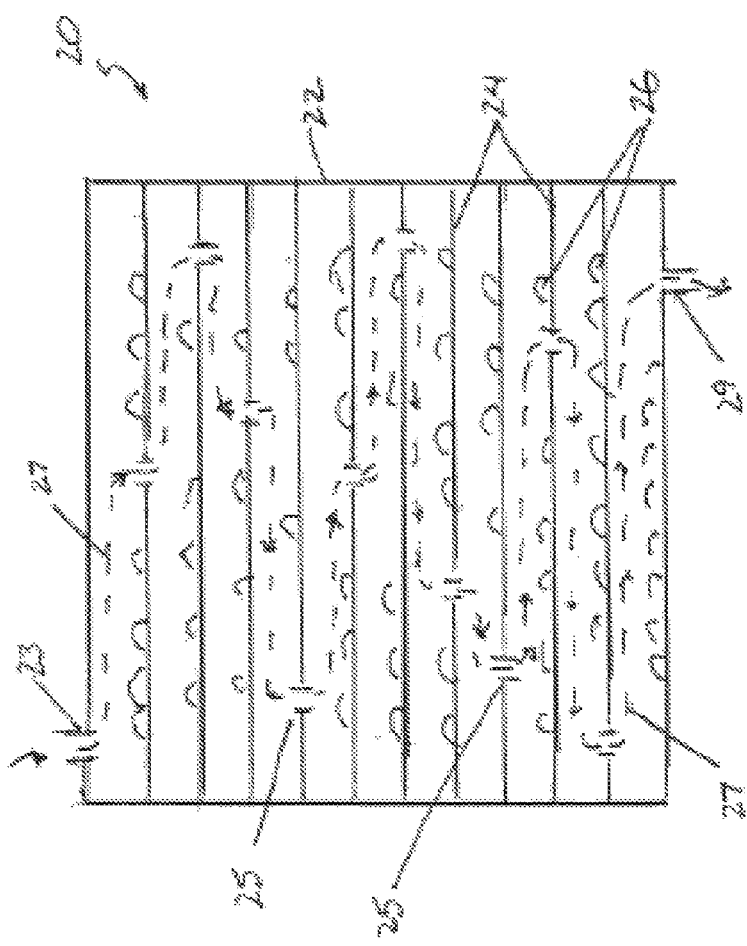
FIG. 2 is a schematic illustration of a stem cell bioreactor for use in a system according to the invention.

FIG. 2 provides a schematic illustration of a stem cell reactor 20 according to the invention including chamber 22, fluid inlet 23, a plurality of substrate surface layers 24 seeded with stem cells 26. Passageways 25 between the layers permits lymphocytes to flow from inlet 23 to outlet 29 along flow path 27. In use, the lymphocytes from the apheresis apparatus of claim 1 are feed into chamber 22 where modulation/activation occurs. After a suitable period of time, the activated Treg cells (and/or other modulated lymphocytes, if any) can be removed from the reactor and returned to the subject.

Figure 3:
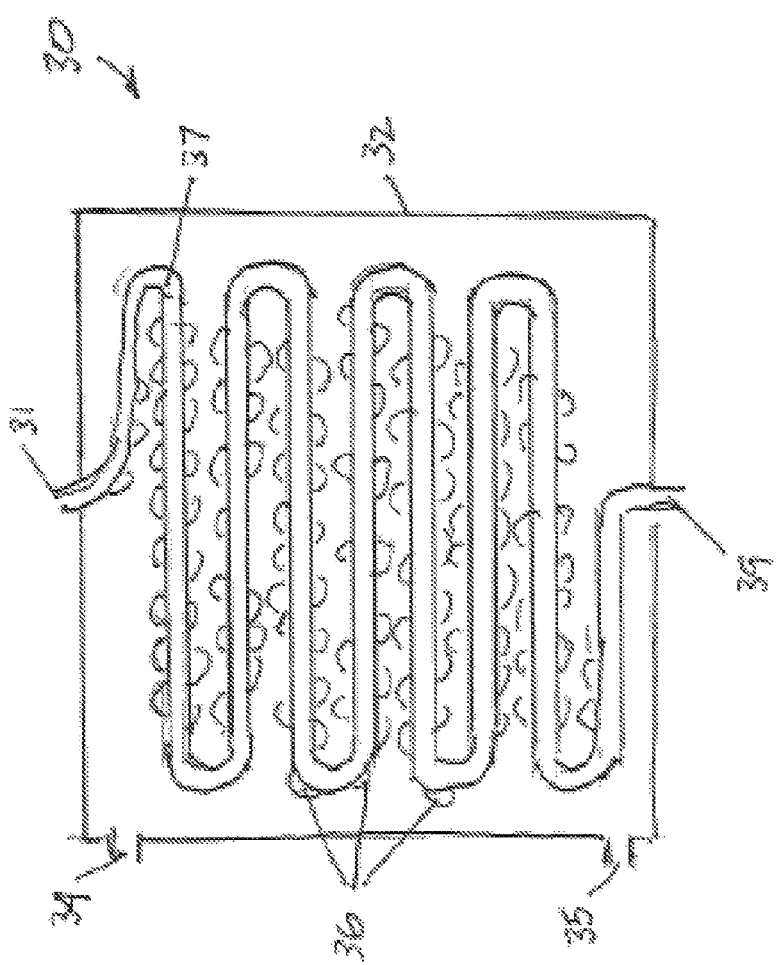
FIG. 3 is a schematic illustration of another embodiment of a stem cell bioreactor for use in a system according to the invention.

FIG. 3 provides a schematic illustration of another embodiment of a stem cell reactor 30 in which the lymphocytes undergoing conditioning are physically isolated from direct contact with the stem cells 36. The reactor 30 includes a chamber 32 housing cultured stem cells. The chamber can have an inlet 34 and outlet 35 for circulating a stem cell nutrient medium. Within the chamber is one or more passageways 37 defined by membranes that isolate the lymphocyte flow path from the stem cells 36, which can be grown anywhere within the chamber, e.g., on the outside of the tubular membrane 37 that isolates the lymphocytes from direct contact with the stem cells. In use, the lymphocytes from the apheresis apparatus of claim 1 are feed into chamber 32 via fluid conduit 31 and removed via fluid conduit 39. While in the chamber, modulation/activation of certain lymphocytes occurs. After a suitable period of time, the activated Treg cells (and/or other modulated lymphocytes, if any) can be removed from the reactor and returned to the subject.

The Examples demonstrate the intrinsic defects of regulatory T lymphocytes (Tregs) for initiation and progression of autoimmune-caused type 1 diabetes (T1D). Therefore, manipulation of lymphocytes is an attractive research focus for developing a successful immunotherapy to prevent and treat autoimmune disorders. Using stem cells, such as CB-SC or PB-SC, can correct functional defects of lymphocytes via the modulation of global gene expression profiles, leading to reversal of overt autoimmune disorders. Notably, co-culturing treatment of lymphocytes and stem cells not only diminishes the autoimmunity. The whole procedure can be simple, safe and cost-effective. The disclosure of such methods and apparatus has potential for clinical impact on diabetes and other autoimmune diseases, paving the way toward a novel therapy of stem cell-modulated lymphocytes to reverse disease in patients.

The present invention further discloses an apparatus for stem cell-based therapy comprising the stem cells of the present invention. In one embodiment, the stem cells of the present invention are used for treating an autoimmune disease and immune disorder-related disease, such as diabetes, in a mammalian subject.

The apparatus can be a bioreactor for suppressing autoreactive lymphocytes. The bioreactor can include a chamber with at least one positively charged substrate surface. A population of stem cells can attach to the substrate surface. The surface can further be in the form of a sheet layer, a plurality of microcarriers and a permeable membrane layer. The substrate surface can also include a hydrophobic substance such as polystyrene or glass which the stem cells can attach to. In one embodiment, the chamber has multiple substrate layers. In one embodiment, the chamber can have at least two layers and as many as 35 or any number therebetween.

The chamber can also allow interaction between the stem cells and mononuclear cells/lymphocytes. The interaction can be through cell-to-cell contact. The interaction may also be through soluble factors released from one cell to another. The chamber can also prevent cell-to-cell contact between the stem cells and mononuclear cells/lymphocytes. A porous membrane can be used to provide a barrier between the stem cells and mononuclear cells/lymphocytes, allowing soluble factors to pass through the membrane but not cells. The porous membrane can have pore sizes sufficiently small to prevent the cells, stem cells, co-cultured population of cells, lymphocytes, T cells, from passing through to the opposite side of the membrane. In another embodiment, the porous membrane has sufficiently large pores to allow passage of stem cell excreted factors, growth factors, cytokines, iNOS, from one side of the membrane to the other. In one embodiment, the stem cells are adhered to one surface of the porous membrane. In another embodiment, the pores are no greater than about half the size of an average stem cell.

The bioreactor can also include an inlet conduit for introducing lymphocytes into the chamber. The inlet conduit can allow a population of cells to flow into the bioreactor through the inlet. The bioreactor can also include an outlet conduit for extracting the treated, co-cultured lymphocytes from the chamber. Gravity and/or pumping can move the population of cells from the inlet to the outlet conduit.

The bioreactor can include a chamber with stem cells. The stem cells can be seeded on the substrate surface in the chamber. Moreover, the stem cells can be present at a concentration of at least $10^7$ cells. The stem cells can be also be seeded at a concentration of at least $10^4$, $10^5$, $10^6$, $10^7$, $10^8$, $10^9$, $10^{10}$ cells. In one embodiment, the stem cells are present at a confluence of at least at least 40%, 50%, 60%, 70%, 80%, 85%, 90% or 95% on the substrate surface. The stem cells can also be grown in the bioreactor to obtain an optimal confluence. In another embodiment, the stem cells are grown to a confluence of at least at least 40%, 50%, 60%, 70%, 80%, 85%, 90% or 95% on the substrate surface.

The stem cells can also be obtained from multiple sources. The stem cells can be autologous to the mononuclear cells/lymphocytes that were extracted. Alternatively, the stem cells can be allogeneic to the mononuclear cells/lymphocytes. Moreover, the stem cells can be derived from peripheral blood, umbilical cord blood, bone marrow cells, splenic cells, thymic cells, lymphnodes, adipocyte tissues and liver cells.

In another aspect, the invention discloses a system for inhibiting an autoimmune disorder. The system can include a fluid conduit for extracting blood from a subject and a fluid conduit for returning the treated lymphocytes to the subject. The system can also include an apheresis apparatus for separating lymphocytes from the extracted blood. The apheresis apparatus can be separate the lymphocytes based on size, weight, centrifugation etc. Moreover, the apheresis apparatus can selectively separate mononuclear cells, lymphocytes, plasma and red blood cells etc. The apheresis apparatus can be a single needle or a double needle procedure. The apheresis apparatus can be a commercial apparatus, such as ALYX system by Baxter (UK), CS3000plus by Baxter (Deerfield, Ill.), MCS+9000 by Haemonetics (Braintree, Mass.) and COBE Spectra® by CaridianBCT (Lakewood, Colo.).

The system for inhibiting an autoimmune disorder also includes a bioreactor for suppressing autoreactive lymphocytes. The bioreactor can include a chamber with at least one positively charged substrate surface. A population of stem cells can attach to the substrate surface. The surface can further be in the form of a sheet layer, a plurality of microcarriers and a permeable membrane layer. The substrate surface can also include a hydrophobic substance such as polystyrene or glass which the stem cells can attach to. In one embodiment, the chamber has multiple substrate layers. In one embodiment, the chamber can have at least two layers and as many as 35 or any number therebetween.

The system can also include a chamber that allows interaction between the stem cells and lymphocytes. The interaction can be through cell-to-cell contact. The interaction may also be through soluble factors released from one cell to another. The chamber can also prevent cell-to-cell contact between the stem cells and lymphocytes. A porous membrane can be used to provide a barrier between the stem cells and lymphocytes, allowing soluble factors to pass through the membrane but not cells. The porous membrane can have pore sizes sufficiently small to prevent the cells, stem cells, co-cultured population of cells, lymphocytes, T cells, from passing through to the opposite side of the membrane. In another embodiment, the porous membrane has sufficiently large pores to allow passage of stem cell excreted factors, growth factors, cytokines, iNOS, from one side of the membrane to the other. In one embodiment, the stem cells are adhered to one surface of the porous membrane. In another embodiment, the pores are no greater than about half the size of an average stem cell.

The system for inhibiting an autoimmune disorder can include a bioreactor with an inlet conduit for introducing lymphocytes into the chamber and an outlet conduit for extracting the treated, co-cultured lymphocytes from the chamber. The bioreactor also can contain a substrate surface with attached stem cells. The stem cells can be present at a concentration of at least $10^7$ cells. The stem cells can be also be seeded at a concentration of at least $10^4$, $10^5$, $10^6$, $10^7$, $10^8$, $10^9$, $10^{10}$ cells. In one embodiment, the stem cells are present at a confluence of at least at least 40%, 50%, 60%, 70%, 80%, 85%, 90% or 95% on the substrate surface. The stem cells can also be grown in the bioreactor to obtain an optimal confluence. In another embodiment, the stem cells are grown to a confluence of at least at least 40%, 50%, 60%, 70%, 80%, 85%, 90% or 95% on the substrate surface.

Figure 12:
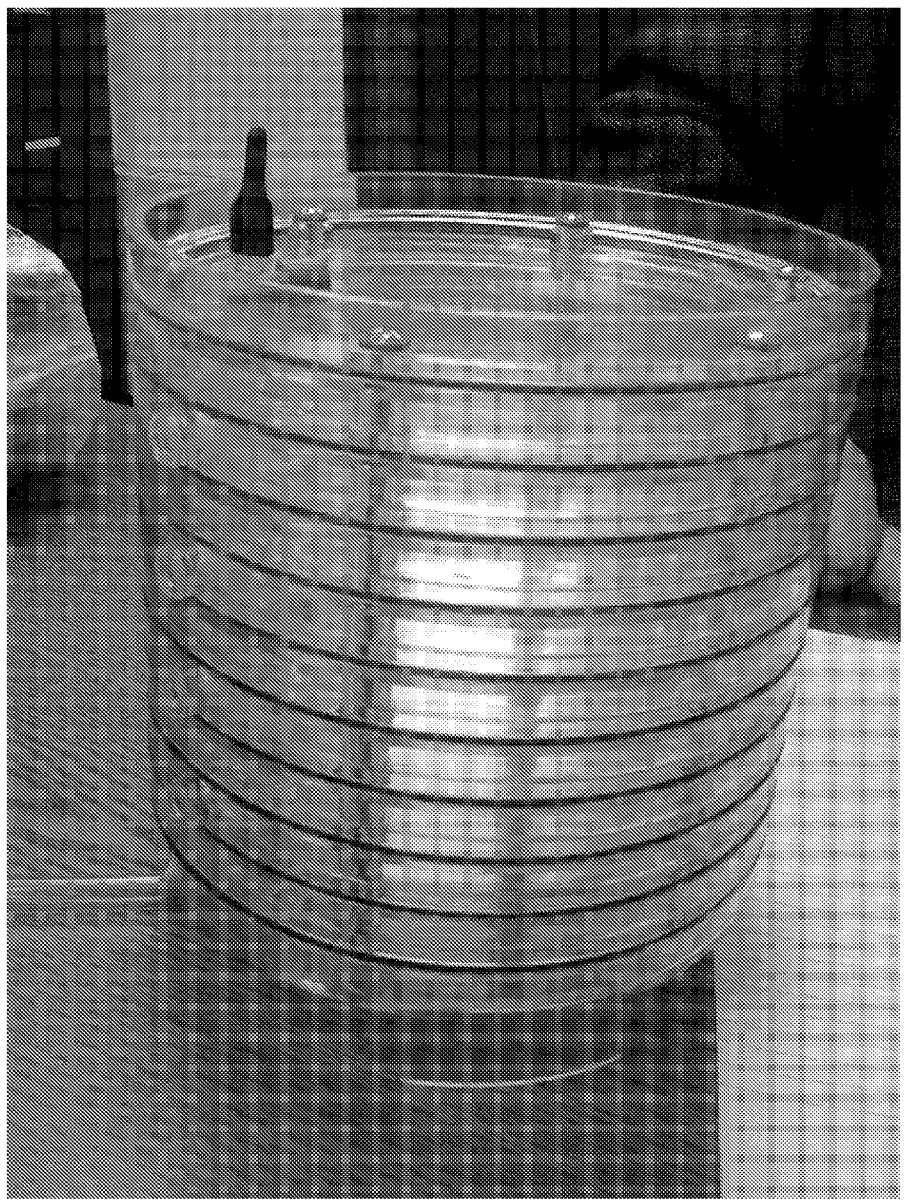
FIG. 12 is an illustration of a stem cell bioreactor for use in a system according to the invention.

The system can also be a closed system that allows for continuous processing of a subject's blood (see FIG. 12). The subject can be connected to the apheresis apparatus through a fluid conduit, such as an intravenous needle. The apheresis apparatus, in turn, separates the lymphocytes from peripheral blood extracted from the subject. The lymphocytes can be introduced to the stem cells in the bioreactor through the inlet conduit. The lymphocytes become activated, capable of suppressing autoreactive lymphocytes such as autoreactive T cells, the treated lymphocytes are extracted from the bioreactor through the outlet conduit and returned to the subject via the fluid conduit.

The stem cell-modulated patient mononuclear cells (e.g., T cells, Tregs, B cells, monocytes, DCs) that are returned to the subject can display different therapeutic potentials, such as systematically modulating an immune balance, inducing immune tolerance in tissues, such as pancreatic islets, reducing inflammation via induction of apoptosis of infiltrated immune cells and stimulating neogenesis of tissue cells, such as replication of pancreatic islet beta cells, followed by overall restoration of pancreatic islet architecture.

EXAMPLES

This invention is further illustrated by the following examples which should not be construed as limiting. The following experiments were performed to demonstrate various aspects of the invention.

Statistical analyses of data in the following examples were performed by the paired Student's t-test to determine statistical significance. Values are given as mean±SD (standard deviation).

Example 1

Methods and Materials

Female NOD/LtJ mice, aged 5-6 weeks, were purchased from Jackson Laboratories (Bar Harbor, Me.) and maintained under pathogen-free conditions at the University of Illinois at Chicago. Blood glucose levels were monitored using an Ascensia ELITE glucometer (Bayer Corporation, Elkhart, Ind.) between 9 and 11 A.M. under nonfasting conditions. Female diabetic NOD/LtJ mice (at 24-28 weeks of age) with spontaneously-developed autoimmune diabetes as confirmed by weight loss, polyuria, and nonfasting blood glucose levels >250 mg/dL for at least 2 consecutive days were used for treatment, according to a protocol approved by the Animal Care Committee (ACC) of University of Illinois at Chicago.

Co-Cultures

Human umbilical cord blood (60-120 ml/unit/bag) was purchased from Life-Source Blood Services (Glenview, Ill.), which were derived from healthy donors. Application of cord blood for our researching does not need the ethical approval from the University and sign any agreements with donors due to their commercial availability. Human cord blood-derived stem cells (CB-SC) were generated as previously described. In brief, cord blood mononuclear cells were plated in 150×15 mm Petri dishes (Becton Dickinson Labware, Franklin Lakes, N.J., not tissue culture-treated dishes) at $1 \times 10^6$ cells/ml, 25 ml/dish in RPMI 1640 medium supplemented with 7% fetal bovine serum (Invitrogen, Carlsbad, Calif.), and incubated at 37° C., in 8% $CO_2$. After 2-3 weeks, CB-SC growing at 80-90% confluence were co-cultured with mouse lymphocytes after removing all unattached cord blood mononuclear cells. For co-culture, mouse lymphocytes were isolated from 6-8 week-old NOD mouse spleens and plated onto CB-SC at a ratio 1:10 of CB-SC:lymphocytes in 150×15 mm Petri dishes containing 25 ml RPMI 1640 medium supplemented with 7% fetal bovine serum (Invitrogen), and incubated at 37° C. in an incubator with 8% $CO_2$. After co-culture for 2-4 days, the suspending lymphocytes were collected for experiments with a minimum CB-SC contamination (<1% of floating cells were positive for a CB-SC marker human leukocyte common antigen CD45). Because CB-SC tightly adhere to the culture dishes and exhibit large rounded morphology, it is easy to distinguish lymphocytes from CB-SC and to collect them. In control experiments, lymphocytes were cultured in identical growth conditions but without CB-SC.

Flow Analysis and Sorting

Flow analysis and cell sorting were performed as previously described. For flow analysis, cells were incubated with rat anti-mouse CD16 monoclonal antibody (eBioscience, San Diego, Calif.) diluted in medium containing 2.5% horse serum (Vector Laboratories) for 15 min at 4° C. to block Fc receptor and to prevent non-specific staining. Cells were incubated with rat anti-mouse monoclonal antibodies (eBioscience), including Alex Fluor® 647-conjugated CD3, FITC- or phycoerythrin (PE)-conjugated CD4, FITC-conjugated CD25, and/or phycoerythrin-Cy7 (PE-Cy7)-conjugated CD62L for 45 min at 4° C. and then washed with cold PBS prior to flow analysis. Isotype-matched rat anti-mouse IgG antibodies (eBioscience) served as negative control. After staining, cells were analyzed using a CyAn ADP (DakoCytomation). For intra-cellular cytokine staining, cells were initially stained for cell surface antigens (e.g., PE-conjugated CD4, FITC-conjugated CD25, and PE-Cy7-conjugated CD62L) and then prepared by using a BD Cytofix/Cytoperm Fixation/Permeabilization kit (BD Biosciences, San Jose, Calif.). Subsequently, cells were stained with different combinations of antibodies including FITC-conjugated IL-4, Alexa Fluor® 647-conjugated IL-10, Alexa Fluor® 647-conjugated IL-12, Pacific blue-conjugated IFN-γ (eBioscience), biotinylated anti-TGF-β1 Ab (Catalog number BAF240, R & D Systems, Minneapolis, Minn.). For TGF-β1 staining, cells were restrained with strepavidin-conjugated FITC (Vector Laboratories). Alexa Fluor 647-conjugated anti-Foxp3 was purchased from eBioscience. For cell sorting to isolate different cell populations CB-SC-co-cultured, and control mouse lymphocytes, or freshly-isolated mouse splenocytes were initially incubated with CD16 Ab to block Fc receptor binding and then incubated with different combination of antibodies such as FITC-conjugated CD4 and PE-Cy7-conjugated CD62L for 45 min at 4° C. and subjected to cell sorting using MoFlo (DakoCytomation). After confirming the purity of the population (>98%), CD4$^+$CD62L$^+$ Tregs were collected and used in different in vitro and in vivo experiments.

Quantitative Real Time PCR

Expression of different mRNAs was analyzed by quantitative real-time PCR. Total RNA was extracted using a Qiagen kit (Valencia, Calif.). First-strand cDNAs were synthesized from total RNA using QuantiTect Reverse Transcription kit according to the manufacturer's instructions (Qiangen, Valencia, Calif.). Real-time PCR was performed on each sample in triplicate using the ABI Prism 7900HT Fast Real-Time PCR System (Applied Biosystems, CA), under the following conditions: 95° C. for 15 min, then 40 cycles of 95° C. for 15 s, and 60° C. for 60 s, using the validated gene-specific RT$^2$ PCR Primer sets for each gene (SuperArray, Frederick, Md.). Expression level of each gene, relative to β-actin as an internal control, was determined. For real-time PCR array, a mouse Th1-Th2-Th3 PCR array kit was used according to the manufacturer's instructions. The data were analyzed using a web-based PCR array data analysis software provided by the manufacturer (SuperArray).

In Vivo Treatment

To treat established diabetic NOD mice, spleen lymphocytes isolated from female NOD mice at 6-8 weeks of age were co-cultured with CB-SC as described above. After co-culture for 2-4 days, floating lymphocytes were collected for cell sorting as described above. The purified CD4$^+$CD62L$^+$ Tregs (mCD4CD62L Tregs, 3×10$^6$ cells) were administered intraperitoneally into overt diabetic NOD mice in 100 µl PBS/mouse (i.p., close to pancreas) for the first dose, followed by a second dose at 2 million cells in 100 µl, PBS/mouse (i.p., close to pancreas) one week later. Diabetic mice injected with same volume of PBS served as one control. Because of a marked decrease in lymphocyte viability after in vitro culture in the absence of CB-SC, the sorted CD4$^+$CD62L$^+$ Tregs from freshly-isolated mouse spleen lymphocytes without co-culture with CB-SC (control CD4CD62L Tregs) served as an additional control. Blood glucose levels and body weights were monitored twice a week until termination of the experiment. Three weeks after initiation of treatment, glucose tolerance testing was done as described below (n=3 for each group). At seven weeks after treatment initiation, control mice were sacrificed for pathology due to severe hyperglycemia (>600 mg/dL) and loss of body weight (>20%). Diabetes-free mice following treatment with mCD4CD62L Tregs were also sacrificed for histological examinations. To measure insulin, blood samples were collected from the tail vein. Blood insulin level was measured using an ultrasensitive mouse insulin enzyme-linked immunosorbent assay (EIA) kit (Alpco Diagnostics, NH) following the manufacturer's protocols. The sensitivity of the assay is 0.019 ng/ml.

Intraperitoneal Glucose Tolerance Testing

Mice were fasted overnight (12 h), weighed and injected intraperitoneally with a bolus of glucose (2 mg/g of body weight). Blood was then drawn from a tail vein at 0, 10, 20, 30, 45, 60, 90, and 120 min after glucose challenge. Glucose levels were measured from whole tail vein blood as described above.

Immunohistochemistry

Pancreata were fixed in 10% formaldehyde, processed, and embedded in paraffin. Serial sections were cut at 5 µm thickness. Immunostaining was performed as previously described with minor modifications. To block non-specific staining, sections were incubated in a buffer containing 2.5% horse serum (Vector Laboratories) for 20 min at room temperature. Primary antibodies included guinea pig polyclonal anti-insulin Ab (DakoCytomation, Carpinteria, Calif.), mouse anti-glucagon mAb (Sigma), mouse anti-TGF-β1 mAb (Catalog number MAB240, 25% cross-reactivity with latent form of TGF-β1, no cross-reactivity with TGF-β2, <2% cross-reactivity with TGF-β3 and TGF-β5, R & D Systems), mouse anti-SMAD4 mAb (Santa Cruz Biotechnology, Santa Cruz, Calif.), rabbit anti-Ki67 mAb and rat anti-macrophage marker F4/80 mAb (Novus Biologicals, Littleton, Colo.), and hamster anti-mouse dendritic cell marker CD11c (BD Pharmingen). Second Abs included Texas red-conjugated AffiniPure donkey anti-guinea pig IgG, rhodamine-conjugated AffiniPure donkey anti-rabbit IgG, AMCA AffiniPure Donkey Anti-Rabbit IgG, FITC-conjugated AffiniPure donkey anti-mouse IgG, and Cy5-conjugated AffiniPure donkey anti-mouse IgG, AMCA AffiniPure Donkey Anti-armenian hamster IgG, and Cy5-conjugated AffiniPure donkey anti-rat IgG (Jackson ImmunoResearch Laboratories, West Grove, Pa.). For non-fluorescence staining, after incubation with primary antibodies, cells were stained with an ABC kit (Vector Laboratories, Burlingame, Calif.). Biotinylated horse anti-rabbit Ab and biotinylated goat anti-guinea Ab were purchased from Vector Laboratories (Burlingame, Calif.). For isotype-matched controls, mouse IgG$_{1κ}$ was purchased from BD Biosciences, guinea pig serum and rabbit IgG from Santa Cruz Biotechnology. For pancreatic slides, we counterstained with hematoxylin (Sigma) after immunostaining. For every experiment, isotype-matched antibodies were used as negative controls. Cells were photographed with a Zeiss Axiocam Color Camera using Zeiss Axioskop Histology/Digital Fluorescence microscope for HRP-immunostaining images, with Zeiss LSM 510 META confocal microscope for fluorescence images.

To compare total β-cell mass after immunostaining with insulin Ab, β-cell mass was measured and calculated by point-counting morphometric analysis using Image J software.

To score insulitis, pancreatic sections from each experimental group were stained with hematoxylin and eosin (H&E staining, Sigma). At least 50 islets from 200 serial sections of each pancreas were examined to evaluate the degree of leukocyte infiltration. Insulitis was graded into five categories based on the extent of intra-islet infiltration of leukocytes: no insulitis (no infiltration), mild insulitis (<25% infiltration), moderate insulitis (25%~50% infiltration), severe insulitis (50%~75% infiltrations), and profound insulitis (>75% infiltration).

To determine apoptosis of infiltrated leukocytes, in situ cell death detection kit (fluorescein) (Roche Applied Science, Indianapolis, Ind.) was applied and performed using the manufacturer's recommended protocol. Cryosections (8 µm thickness) of frozen pancreata from mCD4CD62L Treg-treated diabetic mice and control group were prepared by using Microtome Cryostat HM 5000M (Microm International GmbH). To determine which cell type became apoptotic, we use different markers including PE-conjugated CD4 mAb for CD4$^+$ T cells, PE-conjugated CD8 mAb for CD8$^+$ T cells, PE-conjugated B220 mAb for B cells, and rat anti-mouse F4/80 mAb for macrophages respectively in combination with TUNEL staining. The mAbs to CD4, CD8 and B220 were from eBioscience. Cryosections were initially detected with In Situ Cell Death Detection Kit (Roche), followed by immunostaining with different monoclonal Abs and imaging with a Zeiss LSM 510 META confocal microscope. After double staining, positive cells were quantified directly on the confocal microscope and/or on images. Cryosections incubated with label solution without TUNEL reaction mixture and/or isotype-matched IgG served as negative controls.

Cytokine Assay

Cytokine levels in mouse plasma were quantified using commercial ELISA kits following manufacturer's instructions. We purchased mouse IFN-γ ELISA kit from Biolegend Inc. (San Diego, Calif.), mouse IL-4 and IL-10 ELISA kits from Assay Designs (Ann Arbor, Mich.), and TGF-β1 ELISA kit from Promega (Madison, Wis.).

Example 2

Regulation of Mouse Regulatory T Lymphocytes

To investigate the therapeutic potential of Tregs in T1D, we employed an experimental nonobese diabetic (NOD) mouse model. Initially, we tested the co-culture of CB-SC and NOD mouse spleen-derived lymphocytes and found that co-culture with CB-SC did not significantly stimulate the proliferation of mouse lymphocytes at different ratios of CB-SC:lymphocytes (1:5, 1:10 and 1:20) FIG. 4A, p=0.25, p=0.15, p=0.16 respectively), which is similar to the co-culture of CB-SC and human lymphocytes. Data represented mean±s.d. of four independent experiments.

Next, we analyzed co-cultures of CB-SC and mouse lymphocytes for the presence of Tregs including conventional $CD4^{++}CD25^+$ Treg and $CD4^+Foxp3^+$ Treg, and the $CD4^+CD62L^+$ Treg. We found no significant differences in $CD4^+CD25^+$ Treg and $CD4^+Foxp3^+$ Treg in total mouse spleen lymphocytes that were either cultured alone or with CB-SC. In contrast, the percentage of $CD4^+CD62L^+$ Treg was increased about 5-fold after co-culture with CB-SC, FIG. 4B. Further flow cytometry revealed that only a very small proportion of these $CD4^+CD62L^+$ Tregs was $CD4^+CD25^+CD62L^+Foxp3^+$ positive (FIG. 4C) and this percentage was not different between lymphocytes co-cultured with or without CB-SC (0.11±0.04% vs 0.10±0.03%, P=0.44). We subsequently focused on $CD4^+CD62L^+$ Tregs, which were primarily affected by co-culture with CB-SC (designated CB-SC-modulated $CD4^+CD62L^+$ Tregs, mCD4CD62L Tregs). Data in B-C are representative of three to five experiments.

Figure 4:
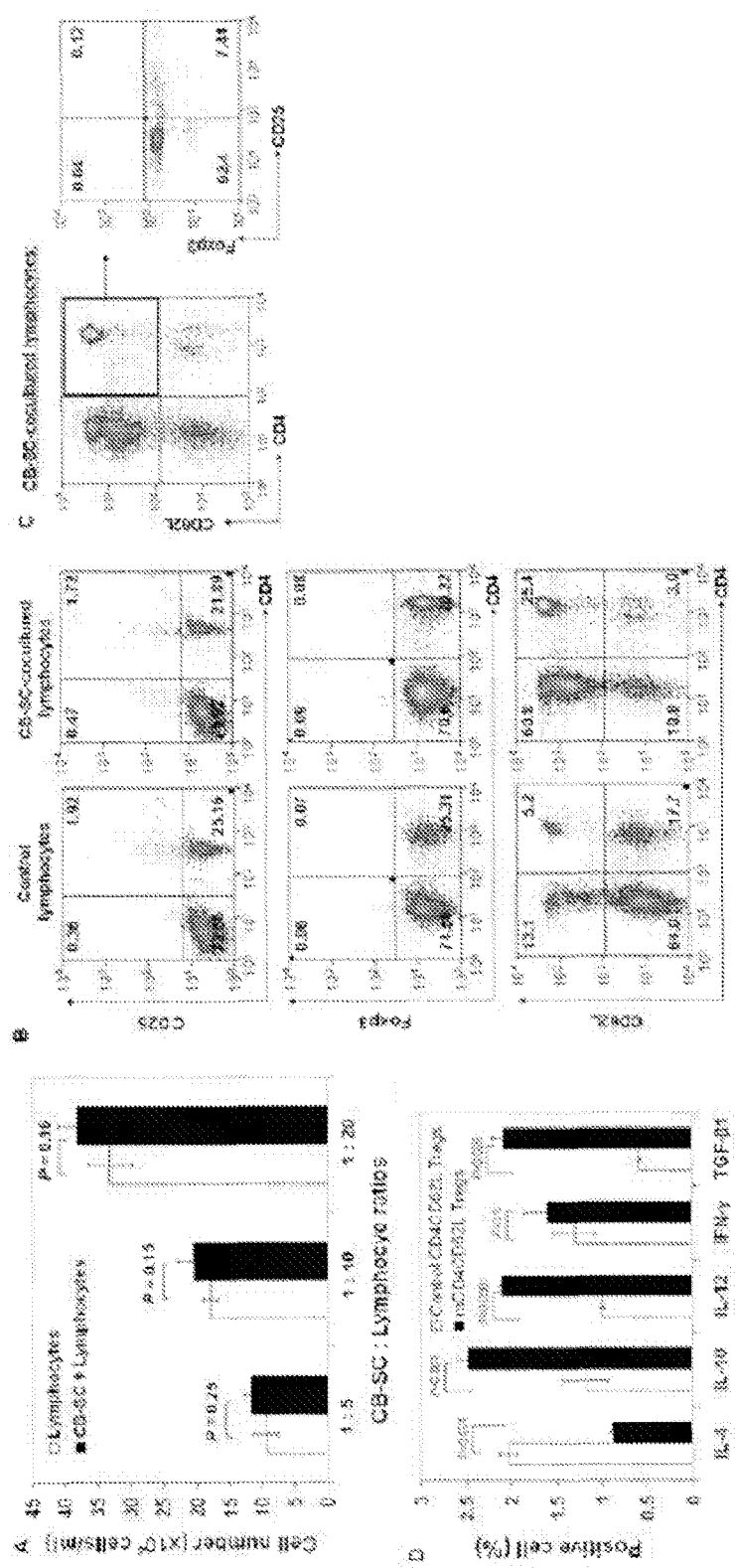
FIG. 4A shows human cord blood stem cells CB-SC display low immunogenicity without stimulating the proliferation of allogeneic lymphocytes.
FIG. 4B shows the percentage of $CD4^+CD25^+$ Treg, $CD4^+$ $Foxp3^+$ Treg, and $CD4^+CD62L^+$ Treg after in vitro co-culture with CB-SC.
FIG. 4C shows flow analysis of CD25 and Foxp3 expressions in $CD4^+CD62L^+$ Tregs after in vitro co-culture with CB-SC.
FIG. 4D shows flow analysis of $CD4^+CD62L^+$ Tregs after intra-cellular cytokine staining. Isotype-matched IgG served as control.

To document modulation of $CD4^+CD62L^+$ Tregs by CB-SC after in vitro co-culture, intracellular cytokines related to helper T (Th)1 and Th2 immune responses were measured using flow analysis (FIG. 4D). Results demonstrated that the IL-4 level was significantly down-regulated (p=0.004), whereas IL-10, IL-12 and TGF-β1 levels were up-regulated in mCD4CD62L Tregs compared with control CD4CD62L Tregs (p=0.001, p=0.0001, and p=0.006 respectively). In contrast, the IFN-γ expression did not change following co-culture with CB-SC (FIG. 4D, p=0.5). Next, we investigated expression of Th1-Th2-Th3 cell-related genes by using quantitative real time PCR array in the purified $CD4^+CD62L^+$ Tregs following co-culture with CB-SC. Results demonstrated that mCD4CD62L Tregs displayed marked down-regulation of Th cell-related genes including multiple cytokines and their receptors, chemokines and their receptors, cell surface molecules, along with signaling pathway molecules and transcription factors. These data clearly indicate that in vitro co-culture with CB-SC causes substantial modifications of gene expression in mouse $CD4^+CD62L^+$ Tregs, specifically for function-related cytokine and chemokine genes.

CB-SC-Modulated $CD4^+CD62L^+$ Tregs Correct Hyperglycemia in Mice

Figure 5:
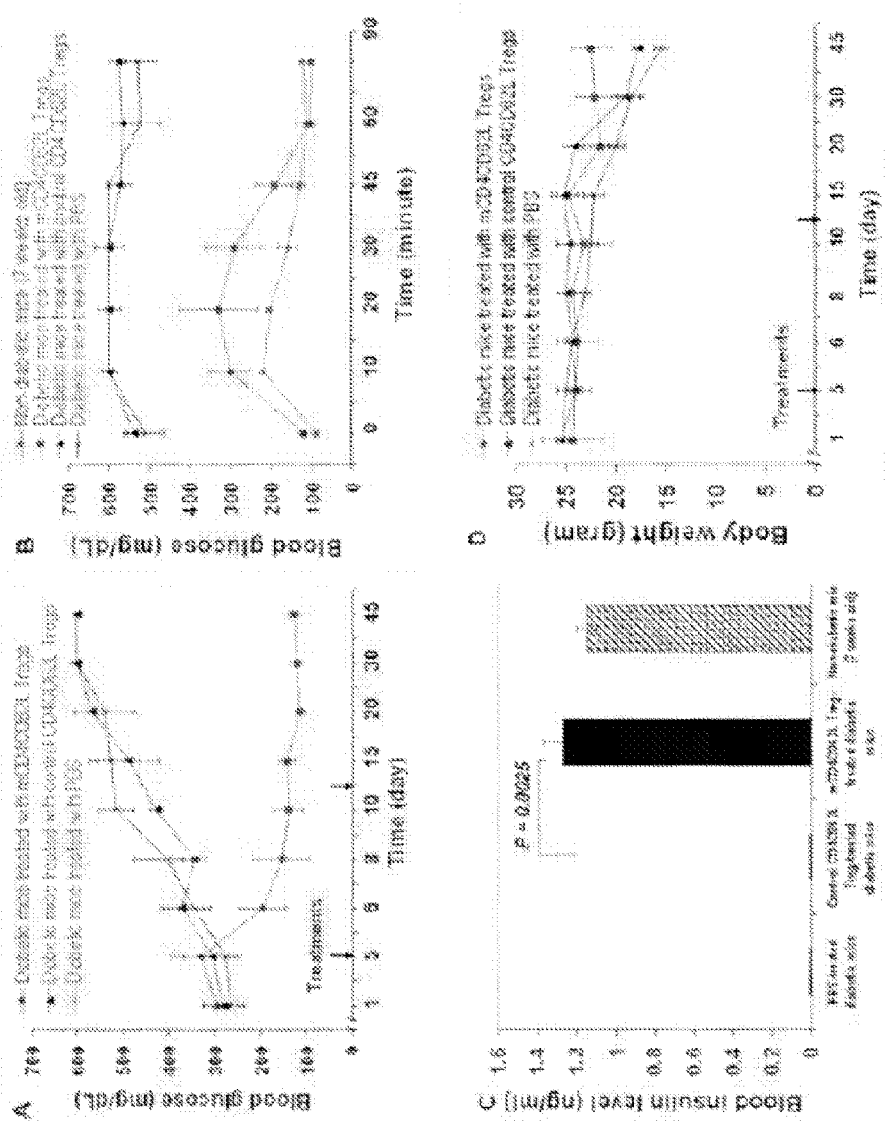
FIG. 5A shows the CB-SC modulated CD4+CD62L+ Treg cells (mCD4CD62L Tregs) can correct hyperglycemia in diabetic NOD mice. Purified control CD4CD62L Tregs served as control (total 5 million cells/mouse, i.p., blue line, n=5 mice). PBS served as an additional control (black line, n=5 mice)
FIG. 5B shows intraperitoneal glucose tolerance testing (IPGTT) 3 weeks following the $1^{st}$ treatment with mCD4CD62L Tregs. Seven-week old NOD mice served as normal control.
FIG. 5C shows determination of blood insulin levels by ELISA.
FIG. 5D shows the effects of treatment on mouse body weight.
FIG. 5E shows the morphometric analysis of pancreatic β-cell mass. Pancreatic β-cell mass was determined by point-counting morphometry on insulin-positive islet β cells followed by immunostaining with guinea pig anti-insulin Ab (Dako) and counter-staining with hematoxylin.
FIG. 5F shows the quantification of Ki67-positive cells in pancreatic islets after double immunostaining with Ki67 and insulin Abs. Isotype-matched rabbit IgG served as control for rabbit anti-Ki67 mAb.
Figure 5:
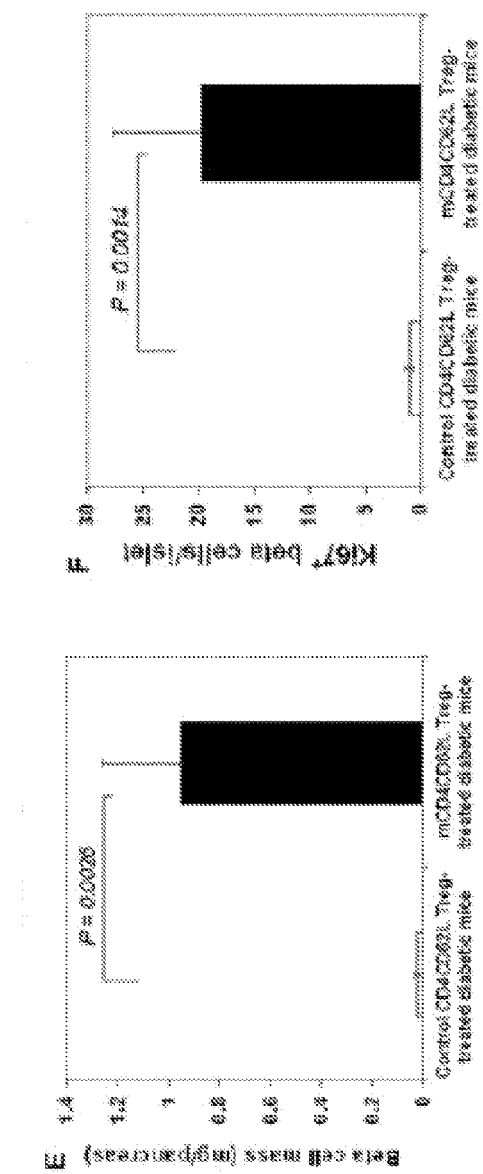

Next, overt diabetic NOD mice (female, at 24-28 weeks of age) were treated with mCD4CD62L Tregs (total 5 million cells/mouse, i.p., n=8 mice) for 5-20 days after the diagnosis of T1D to determine their therapeutic potential. The control CD4CD62L Tregs at the same cell amount (i.p., n=5 mice) and vehicle PBS (total 200 μl/mouse, i.p., n=5 mice) served as controls. Notably, we found that treatment with mCD4CD62L Tregs restored euglycemia in these overt diabetic mice (6/8 mice) (FIG. 5A). However, treatment with control CD4CD62L Tregs or PBS failed to reduce hyperglycemia in diabetic mice (5/5, 5/5 mice respectively) (FIG. 5B). Diabetic mice that had been rendered euglycemic after treatment with mCD4CD62L Tregs also showed an improved glucose tolerance test (IPGTT), similar to that of non-diabetic NOD mice at 7 weeks (FIG. 5B). However, diabetic mice treated with PBS or control CD4CD62L Tregs maintained high glucose levels (>500 mg/dL) without any observable down-regulation (FIG. 5B). Moreover, we monitored blood insulin levels 6 weeks after treatment with mCD4CD62L Tregs. Results showed that insulin in diabetic mice treated with control CD4CD62L Tregs or PBS vehicle was undetectable by ELISA (0.019 ng/ml sensitivity for the ELISA kit, FIG. 5C). These mice had to be sacrificed because of severe hyperglycemia (BG>600 mg/dL) and loss of body weight (>20%) according to the protocol approved by the Animal Care Committee (FIG. 5D). In contrast, blood insulin levels in diabetic NOD mice treated with mCD4CD62L Tregs were significantly increased (FIG. 5D, p=0.0025).

At 45 days after treatment, we subjected pancreata to histological analysis and evaluated total β-cell mass followed by immunostaining with insulin Ab on serial pancreatic sections. Morphometric analysis demonstrated that treatment with mCD4CD62L Tregs significantly increased total β-cell mass (FIG. 5E, p=0.0026). In contrast, β-cell mass was markedly lower after vehicle PBS treatment or control CD4CD62L Treg treatment (FIG. 5E). To understand the mechanism of the increase in total β-cell mass, we determined the expression of a cell proliferation nuclear marker Ki67 in pancreatic islets. Double immunostaining with insulin and Ki67 Abs revealed that 20±8 β cells/islet expressed Ki67 in pancreatic islets of mCD4CD62L Treg-treated mice (FIG. 5F), which was much higher than that in pancreatic islets of mice treated with control CD4CD62L Tregs (1±0.4) (p=0.0014). It suggests that de novo proliferation of β cells accounts for the noted increase in total β cell mass. Moreover, double immunostaining with β-cell-marker insulin and α-cell-marker glucagon revealed that pancreatic islets in diabetic mice treated with mCD4CD62L Tregs displayed a similar pattern of α- and β-cell distribution as that noted in normal islets of non-diabetic NOD mice. However, islet architecture was completely destroyed with almost complete disappearance of β cells in the diabetic mice treated with control CD4CD62L Tregs. Thus, treatment with mCD4CD62L Tregs can correct hyperglycemia of T1D mice by promoting β-cell regeneration and reconstitution of islet cell architecture.

Reversal of Insulitis and Immune Dysfunction in NOD Mice

Figure 6:
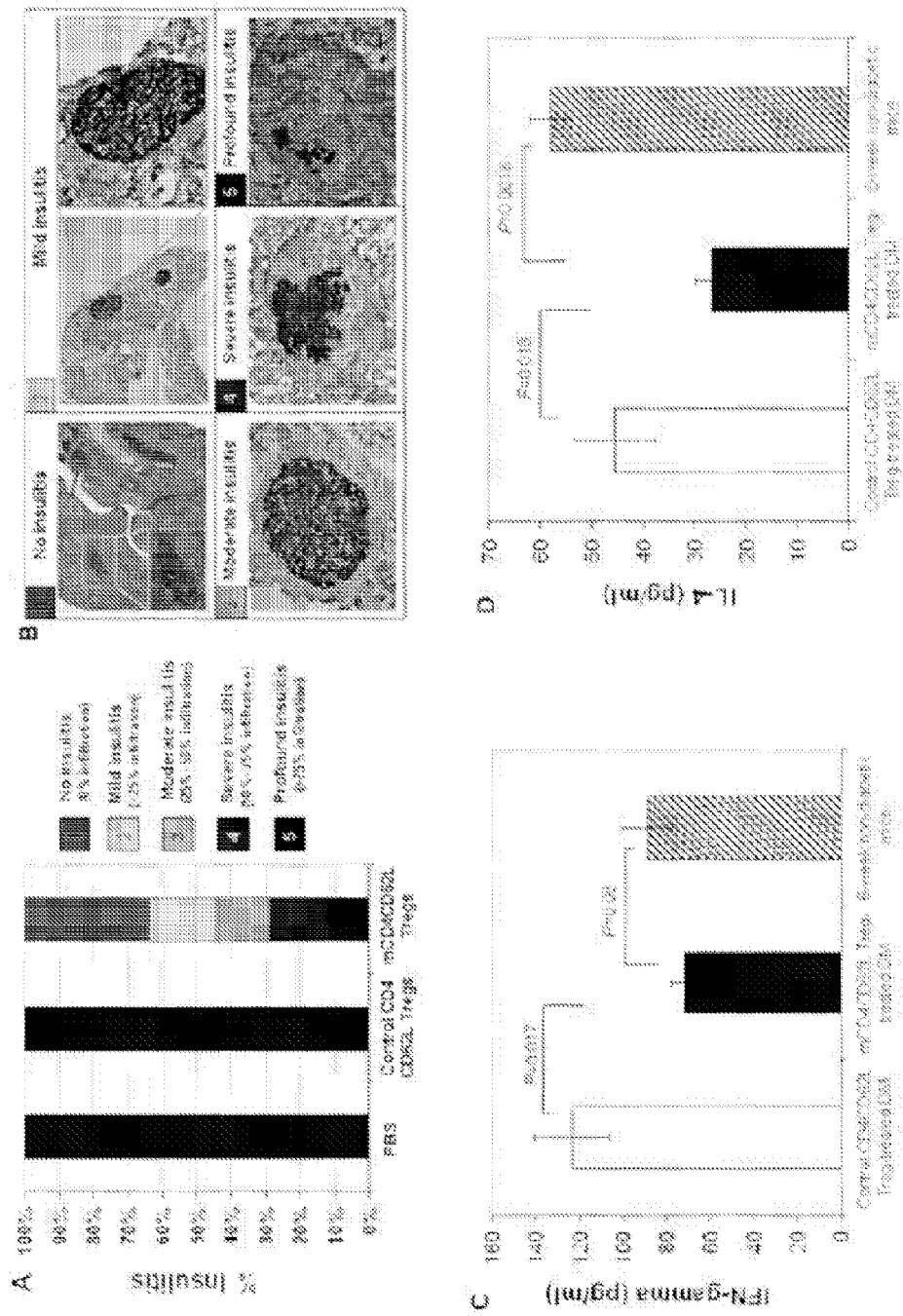
FIG. 6A shows treatment with mCD4CD62L Tregs can reverse insulitis and immune dysfunction in diabetic NOD mice. Treatment with mCD4CD62L Tregs corrects insulitis in overt type 1 diabetic NOD mice.
FIG. 6B shows representative images for different type of insulitis. Data were collected from mCD4CD62L Treg-treated diabetic NOD mice. Scale bar, 50 μm.
FIG. 6C shows the determination of plasma IFN-γ level by ELISA in mice at age of 6 weeks.
FIG. 6D shows the measurement of plasma IL-4 level by ELISA.
FIG. 6E shows the determination of plasma IL-10 level measured by ELISA.
FIG. 6F shows the determination of plasma TGF-β1 level measured by ELISA.
Figure 6:
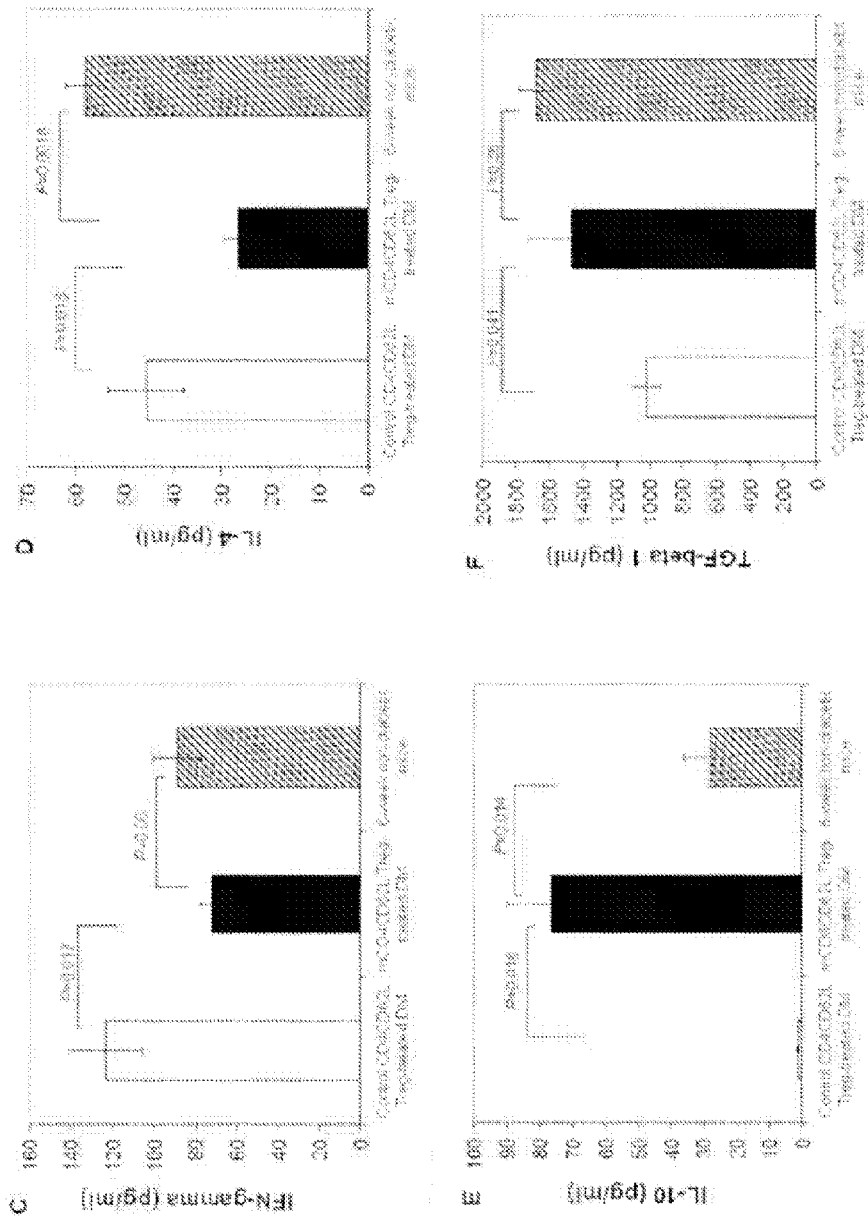

To establish whether mCD4CD62L Tregs exert an immunosuppressive influence on autoreactive effector T cells, we performed pancreatic histological analysis and scored insulitis at 45 days after treatment. Histological evaluations showed that approximately 80% of islet β cells (profound insulitis) were destroyed in diabetic NOD mice prior to treatment. Six weeks post treatment, we found that in diabetic mice receiving mCD4CD62L Tregs, 36% of islets had no or few signs of infiltration of inflammatory cells; 20% of islets displayed mild insulitis; 15% of islets exhibited moderate insulitis; 18% of islets had severe insulitis and only 11% of islets showed profound insulitis (FIGS. 6A and 6B). The insulitis-free islets were of smaller size and positive for the proliferation marker Ki67 (data not shown), suggesting that these islets may have been newly generated. In contrast, all pancreatic islets in diabetic mice receiving control CD4CD62L Tregs showed massive infiltration of inflammatory cells and severe destruction of pancreatic architecture (FIG. 6B), and had few or no insulin-positive cells present. Similarly, pancreatic histological examination demonstrated that those two mice (2/8 mice) that were resistant to mCD4CD62L Tregs treatment also displayed profound insulitis (data not shown) after 45 days observation. Representative data are from 6 diabetic mice (6/8 mice) sensitive to mCD4CD62L Treg treatment with euglycemia. Pancreatic islets were scored for percent of mononuclear cell infiltration after immunostaining for insulin and counter-staining with hematoxylin.

To understand the molecular mechanism underlying reduction of insulitis, we measured plasma Th1/Th2 cytokine levels by ELISA. We found that Th1 cytokine IFN-γ and Th2 cytokine IL-4 were considerably reduced in the plasma of mCD4CD62L Treg-treated diabetic mice relative to control CD4CD62L Treg-treated diabetic mice (P=0.017, FIG. 6C, P=0.018, FIG. 6D, respectively). In contrast, diabetic mice receiving mCD4CD62L Tregs showed a marked increase in plasma IL-10 level compared with those treated with control CD4CD62L Tregs (P=0.016) and non-diabetic NOD mice at age of 6 weeks (P=0.014). Data are shown as mean±s.d. of mouse plasma cytokine levels from three experiments. Additionally, plasma TGF-β1 level was significantly elevated in mCD4CD62L Treg-treated diabetic mice compared with control CD4CD62L Treg-treated diabetic mice (P=0.041). These data suggest that both IL-10 and TGF-β1 may contribute to an induction of immune tolerance after treatment with mCD4CD62L Tregs. These data demonstrate that exposure to CB-SC induced profound changes in mCD4CD62L Tregs that helped restore "normal" islet architecture and β-cell function resulting in the suppression of diabetes.

Figure 7:
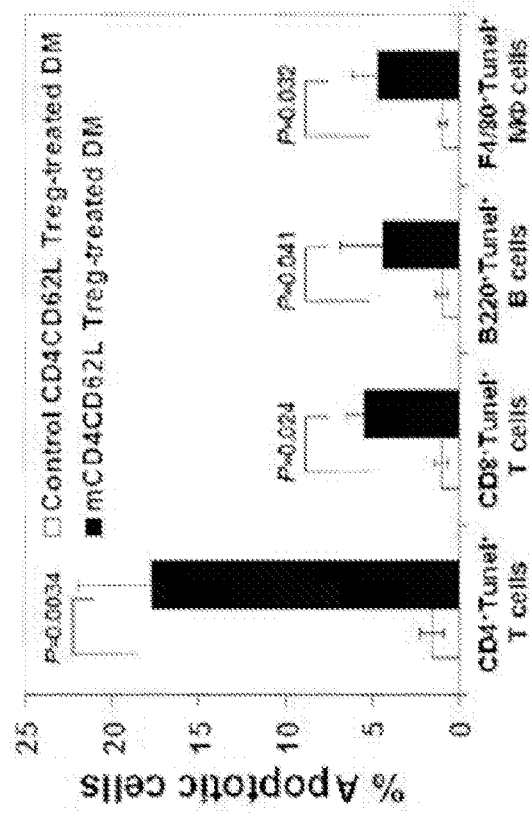
FIG. 7 shows the apoptotic results of infiltrated immune cells in pancreatic islets from treatment with mCD4CD62L Tregs by enhancing expression of TGF-β1 in pancreatic islets.

TGF-β1 is one of the best characterized cytokines contributing to the induction of immune suppression and maintaining of self-tolerance. To elucidate de novo molecular mechanism underlying the protection of islet β cells following treatment with mCD4CD62L Tregs, we determined TGF-β1 expression in pancreatic islets by immunohistochemistry in addition to plasma TGF-β1 measurement. Results demonstrated that TGF-β1 was presented at higher level in pancreatic islets of mCD4CD62L Treg-treated diabetic mice compared with control CD4CD62L Treg-treated diabetic mice. Staining of TGF-β1-positive cells showed two patterns: one was distributed among islet β cells, with average positive cell number of 14±9 cells/islet, and another was located around islet β cells. Importantly, we found that these surrounding TGF-β1-positive cells (negative for macrophage marker F4/80, but positive for dendritic cell marker CD11c, data not shown), along with their released TGF-β1 in the matrix (faint staining), formed a ring surrounding pancreatic islets. This ring may protect newly-generated islets against attack by inducing apoptosis of auto-aggressive effector lymphocytes, as determined by terminal deoxynucleotidyl transferase dUTP nick end labeling (TUNEL) staining (58±23 TUNEL$^+$ infiltrated leukocytes in mCD4CD62L Treg-treated group vs. 9±3 TUNEL$^+$ infiltrated leukocytes in control CD4CD62L Treg-treated group, p=0.02). To clarify which cell type became apoptotic, we performed double staining with different cell markers including CD4 for CD4$^+$ T cells, CD8 for CD8$^+$ T cells, B220 for B cells, and F4/80 for macrophages respectively in combination TUNEL staining. We found that treatment with mCD4CD62L Tregs increased the apoptosis of infiltrated T cells, B cells, and macrophages compared with control CD4CD62L Treg treatment (p=0.0034, p=0.024, p=0.041, and p=0.032 respectively). In comparison with the other three cell types however, CD4$^+$ T cells showed a much higher percentage of apoptotic cells (FIG. 7). Thus, these data suggest that treatment with mCD4CD62L Tregs enhances expression of TGF-β1 in pancreatic islets that may contribute to local protection of newly-generated pancreatic islets from the re-destruction of autoreactive immune cells. Data represent mean±s.d. of five experiments.

Example 3

In Vitro Immune Modulation

Figure 8:
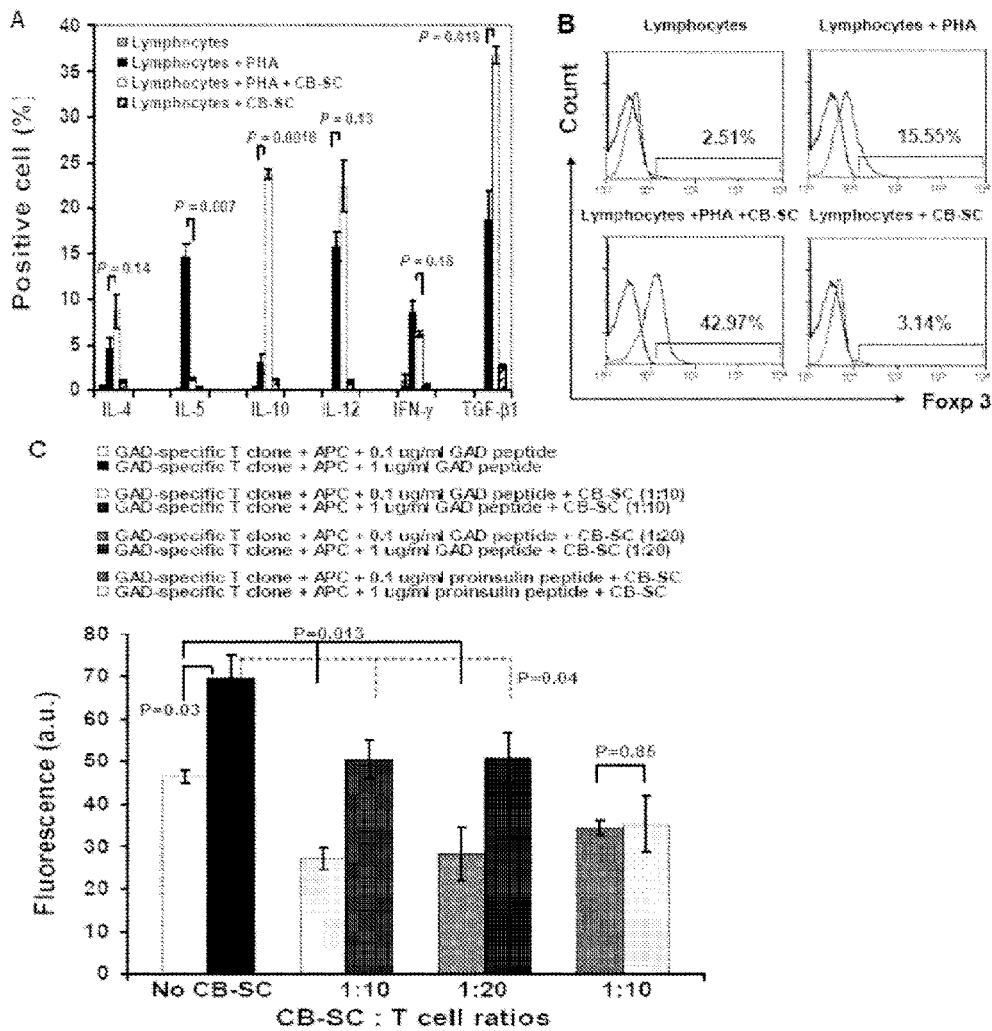
FIG. 8 shows lymphocytes isolated from T1D patients co-cultured with CB-SC at a ratio of 1:10 CB-SC to lymphocytes in the presence or absence of 10 μg/ml PHA. After 24 hrs, floating lymphocytes were collected for flow analyses (A and B).

CB-SC can modulate the function of CD4+CD62L+ Tregs leading to prevention and reversal of overt autoimmune-caused type 1 diabetes (T1D) in NOD mouse model. We examined the immune modulation of CB-SC on CD4+CD62L+ Tregs of T1D patients in the presence of mitogen PHA (FIG. 8A and FIG. 8B). Intra-cellular cytokine staining results demonstrated that IL-5 level was significantly down-regulated (p=0.007), whereas IL-10 and TGF-1 were up-regulated in CD4+CD62L+ Tregs after co-culture with CB-SC compared with control PHA treatment (p=0.0018 and p=0.019 respectively), consistent with those in NOD mouse CD4+CD62L+ Tregs. In contrast, the IL-4, IL-12, and IFN- expressions did not change following co-culture with CB-SC (FIG. 8A). Additionally, transcription factor Foxp3, a specific marker for Tregs, was also up-regulated 2.7 fold after treatment with PHA+CB-SC compared with control PHA treatment (FIG. 8B). Thus, these data indicate that CB-SC can modulate the CD4+CD62L+ Tregs of T1D patients.

To determine the therapeutic potential of CB-SC in T1D, we explore the direct modulation of CB-SC on islet-cell GAD-specific CD4+ T cell clones generated from T1D patients. Results demonstrated that the proliferation of this T cell clone stimulated with antigen-presenting cells (APC) and different dose of GAD peptide were markedly and specifically decreased in the presence of CB-SC compared to control group in the absence of CB-SC (FIG. 8C). Thus, it indicates that CB-SC have a potential to eliminate the pathogenic T cells. Data are shown as mean standard deviation from three independent experiments.

Carboxypeptidase M (CPM) and Brandykinin B1 Receptor

Figure 9:
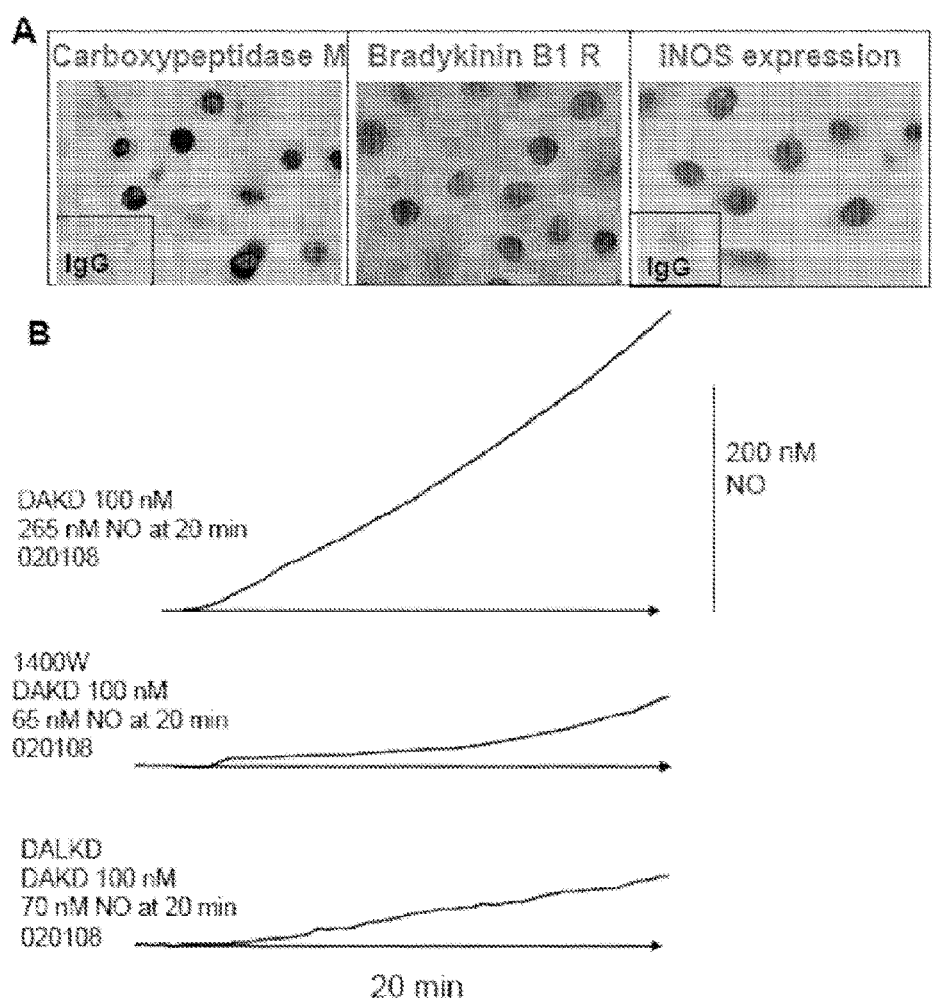
FIG. 9A shows expression of CPM, B1R and iNOS on CB-SC. Isotype-matched IgG served as controls for immunostaining. Magnification, 400.
FIGS. 9B and 9C show real time assay for NO production.
FIG. 9D shows co-culture experiments of mitogen PHA-stimulated lymphocytes co-cultured with CB-SC in the presence of CPM inhibitor MGTA (10 μM) and B1R antagonist DALKD (2 μM)
Figure 9:
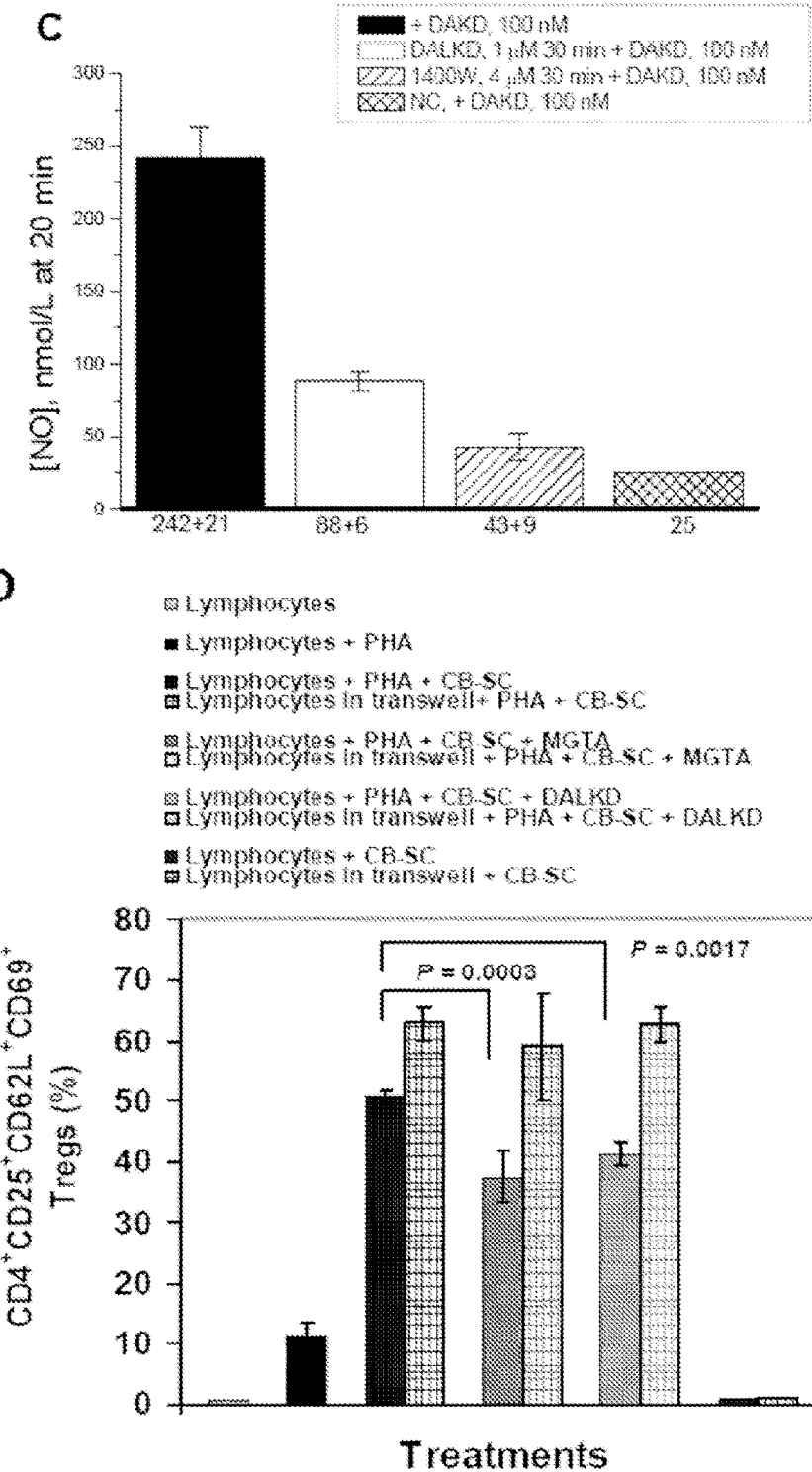

We found that CB-SC expressed membrane carboxypeptidase M (CPM), brandykinin B1 receptor, and inducible nitric oxide synthase (iNOS) (FIG. 9A). Carboxypeptidase M-mediated generation of Arginine substrate for iNOS was shown to enhance NO production in macrophages and endothelial cells. Results showed that NO production was increased in the presence of B1R activator des-Arg 10-bradykinin (DAKD), but inhibited in combination with iNOS specific inhibitor 1400 W or a selective B1 receptor antagonist [Des-Arg10, Leu9] kallidin (DALKD) (FIG. 9B and FIG. 9C). Blocking with the specific B-type carboxypeptidase inhibitor, 2-mercaptomethyl-3-guanidinoethylthiopropanoic acid (MGTA) could block NO production in CB-SC and reverse the suppression of CB-SC on allogeneic lymphocytes, similar to using iNOS inhibitor 1400 W.

To examine the cell-cell contacting effects and CPM and B1R contribution to immune modulation of CB-SC on human Tregs, we performed co-culture experiments in the presence of CPM specific inhibitor MGTA and B1R specific inhibitor DALKD. Lymphocytes plated in trans-wells served as controls. Results demonstrated that blocking CPM and/or B1R could decrease the positive percentage of CD4+CD25+ CD62L+CD69+ Tregs (FIG. 9D). Data are representative of five experiments.

Autoimmune Regulator (Aire) Expression in CB-SC

Figure 10:
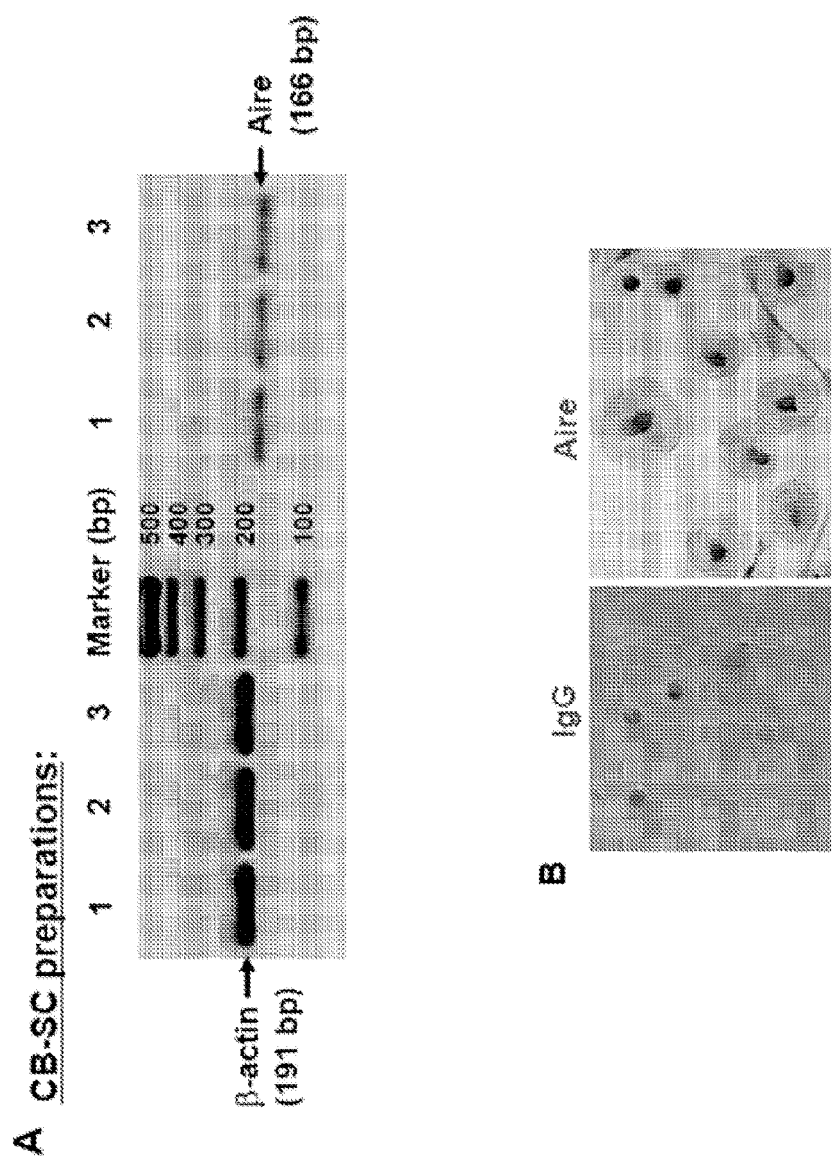
FIG. 10A shows real time PCR analysis for Aire gene, followed by electrophoresis in 2% agarose gel.
FIG. 10B shows immunocytochemistry for transcription factor Aire. Isotype-matched IgG served as control (left) for AIRE staining (right) with magnification 200. Data are representative of eight CB-SC preparations.

The Aire plays an important role in immune tolerance by mediating the ectopic expression of peripheral self-antigens and the deletion of auto-reactive T cells. To explore molecular mechanisms underlying the immune modulation of CB-SC, we found CB-SC express Aire at both gene (FIG. 10A) and protein levels (FIG. 10B). It suggests that Aire in CB-SC may contribute to the immune modulation. Data are representative of three CB-SC preparations.

Figure 11:
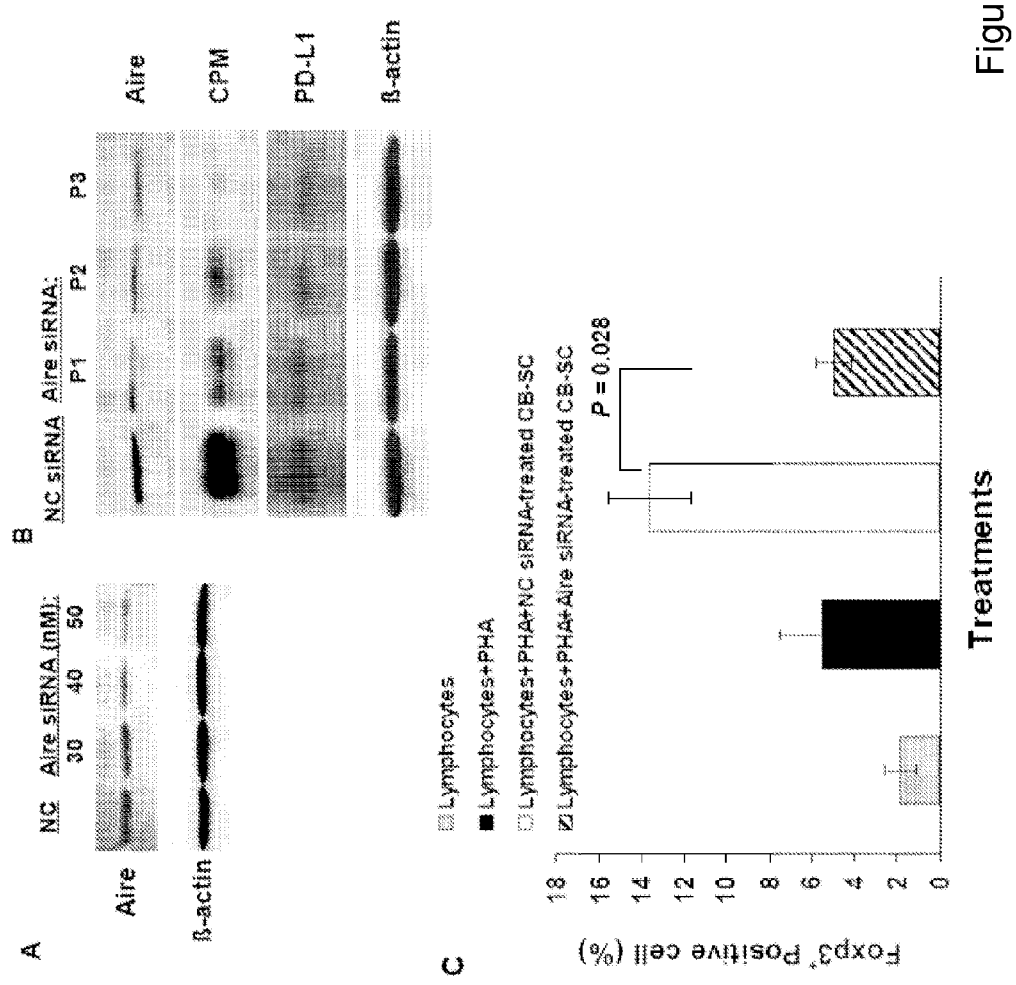
FIG. 11A shows dose responses of Aire siRNA, as shown by Western Blot. Negative control siRNA (NC) at 40 nM served as control.
FIG. 11B shows a western blot with three pairs of Aire-specific siRNA (P1, P2 and P3) could knockdown the protein levels of AIRE, CPM and PD-LI expression with beta-actin serving as an internal control.
FIG. 11C shows flow analysis on Foxp 3 expression. Lymphocytes isolated from adult peripheral blood were co-cultured with CB-SC at ratio of 1:10 of lymphocytes:CB-SC, in the presence of 50 nM Aire siRNA and negative control (NC) siRNA. After PHA stimulation for 24 hours, cells were collected for flow analysis.

To explore the action of Aire in CB-SC, three pairs of Aire-specific siRNA have been administered to knockdown Aire gene expression by using Lipofectamine RNAiMAX (Invitrogen) (FIG. 11A). Data are representative of five CB-SC preparations. Western blot revealed that 70% of Aire protein can be knockdown in the presence of 50 nM aire siRNA in compare with negative control siRNA (FIG. 11B). Notably, western blotting also demonstrated that CPM and PD-L1 protein were also down-regulated in the in the presence of aire siRNA. Western blot also shows the down-regulation of CPM and PD-L1 protein (FIG. 11B). It implies that Aire may regulate their gene expressions at transcriptional levels. Data are representative of three experiments.

To further examine the Aire contribute the immune modulation, we tested human Treg marker Foxp3 in the presence of Aire siRNA and negative control siRNA. Flow analysis demonstrated that expression of Foxp3 was markedly decreased in the presence of Aire siRNA relative to control siRNA (p=0.028, FIG. 11C). Thus, these data indicate that Aire expression in CB-SC contribute to the immune modulation. Data represent mean SD of three experiments.

While the present invention has been described in terms of specific methods and compositions, it is understood that variations and modifications will occur to those skilled in the art upon consideration of the present invention. Those skilled in the art will appreciate, or be able to ascertain using no more than routine experimentation, further features and advantages of the invention based on the above-described embodiments. The practice of the present invention will employ and incorporate, unless otherwise indicated, conventional techniques of cell biology, cell culture, molecular biology, microbiology, genetic engineering, and immunology, which are within the skill of the art. While the present invention is described in connection with what is presently considered to be the most practical and preferred embodiments, it should be appreciated that the invention is not limited to the disclosed embodiments, and is intended to cover various modifications and equivalent arrangements included within the spirit and scope of the claims. Modifications and variations in the present invention may be made without departing from the novel aspects of the invention as defined in the claims. Accordingly, the invention is not to be limited by what has been particularly shown and described. All publications and references are herein expressly incorporated by reference in their entirety.

---

What is claimed is:

1. A bioreactor for modulating lymphocytes and suppressing autoreactive T cells, comprising:
   a chamber having at least one positively charged and hydrophobic substrate surface;
   a population of stem cells attached to the substrate surface, wherein the stem cells are characterized by: (a) displaying embryonic stem cell characteristics; (b) displaying hematopoietic cell characteristics as being positive for leukocyte common antigen CD45; (c) not expressing the CD34 marker; (d) displaying low immunogenicity; and (e) expressing autoimmune regulator;
   an inlet conduit for introducing lymphocytes into the chamber for co-culturing with the stem cells, and the lymphocytes are free from plasma before being introduced into the chamber; and
   an outlet conduit for extracting the lymphocytes following co-culturing with the stem cells.

2. The bioreactor of claim 1, wherein the substrate surface comprises at least one sheet layer.

3. The bioreactor of claim 1, wherein the substrate surface comprises a plurality of microcarriers.

4. The bioreactor of claim 1, wherein the substrate surface comprises at least one permeable membrane layer.

5. The bioreactor of claim 1, wherein the substrate surface comprises hydrophobic polystyrene.

6. The bioreactor of claim 1, wherein the stem cells exhibit a confluence of at least 50% on the substrate surface.

7. The bioreactor of claim 1, wherein the stem cells exhibit a confluence of at least 80% on the substrate surface.

8. The bioreactor of claim 1, wherein the stem cells exhibit a confluence of at least 90% on the substrate surface.

9. The bioreactor of claim 1, wherein the chamber is constructed to permit cell-to-cell contact between the stem cells and the lymphocytes.

10. The bioreactor of claim 1, wherein the chamber is constructed to prevent cell-to-cell contact between the stem cells and the lymphocytes.

11. The bioreactor of claim 1, wherein the stem cells are obtained from umbilical cord blood.

12. The bioreactor of claim 1, wherein the stem cells are obtained from peripheral blood.

13. The bioreactor of claim 1, wherein the stem cells are allogenic to the lymphocytes.

14. The bioreactor of claim 1, wherein the stem cells are autologous to the lymphocytes.

15. The bioreactor of claim 1, wherein a population of at least $10^6$ stem cells are present within the chamber.

16. The bioreactor of claim 1, wherein the stem cells are present within the chamber in a ratio to the lymphocytes of at least 1:10.

17. The bioreactor of claim 1, wherein the stem cells are cultured onto multiple substrate surface layers within the chamber.

18. A method of activating regulatory T (Treg) cells comprising the steps of: introducing Treg cells into a bioreactor of claim 1; exposing the Treg cells to stem cells attached to the substrate surface in the chamber of the bioreactor, wherein the stem cells express carboxypeptidase M (CPM); and co-culturing Treg cells with the stem cells.

19. A method of activating regulatory T (Treg) cells comprising the steps of: introducing Treg cells into a bioreactor of claim 1; exposing the Treg cells to a stem cells attached to the substrate surface in the chamber of the bioreactor, wherein the stem cells express brady kinin B1 receptor; and co-culturing Treg cells with the stem cells.

20. A method of activating regulatory T (Treg) cells comprising the steps of: introducing Treg cells into a bioreactor of claim 1; exposing the Treg cells to stem cells attached to the substrate surface in the chamber of the bioreactor, wherein the stem cells express autoimmune regulator (AIRE) protein; and co-culturing Treg cells with the stem cells.

21. A system for inhibiting an autoimmune disorder, comprising:
   a fluid conduit for extracting blood from a subject;
   an apheresis apparatus for separating lymphocytes from the extracted blood, thereby separating the lymphocytes from plasma;
   a bioreactor comprising a chamber having at least one positively charged and hydrophobic substrate surface such that a population of stem cells can be attached to the substrate surface, an inlet conduit for introducing lymphocytes into the chamber, and an outlet conduit for extracting the lymphocytes following co-culturing with the stem cells; and
   a fluid conduit for returning the lymphocytes to the subject, wherein the stem cells are characterized by: (a) displaying embryonic stem cell characteristics; (b) displaying hematopoietic cell characteristics as being positive for leukocyte common antigen CD45; (c) not expressing the CD34 marker; (d) displaying low immunogenicity; and (e) expressing autoimmune regulator.

22. The system of claim 21, wherein the substrate surface of the bioreactor comprises at least one sheet layer.

23. The system of claim 21, wherein the substrate surface of the bioreactor comprises a plurality of microcarriers.

24. The system of claim 21, wherein the substrate surface of the bioreactor comprises at least one permeable membrane layer.

25. The system of claim 21, wherein the substrate surface of the bioreactor comprises hydrophobic polystyrene.

26. The system of claim 21, wherein the stem cells attached to the substrate surface exhibit a confluence of at least 50%.

27. The system of claim 21, wherein the stem cells attached to the substrate surface exhibit a confluence of at least 80%.

28. The system of claim 21, wherein the stem cells attached to the substrate surface exhibit a confluence of at least 90%.

29. The system of claim 21, wherein the chamber of the bioreactor is constructed to permit cell-to-cell contact between the stem cells and the lymphocytes.

30. The system of claim 21, wherein the chamber of the bioreactor is constructed to prevent cell-to-cell contact between the stem cells and the lymphocytes.

31. The system of claim 21, wherein the stem cells attached to the substrate surface are obtained from umbilical cord blood.

32. The system of claim 21, wherein the stem cells attached to the substrate surface are obtained from peripheral blood.

33. The system of claim 21, wherein the stem cells attached to the substrate surface are allogenic to the lymphocytes.

34. The system of claim 21, wherein the stem cells attached to the substrate surface are autologous to the lymphocytes.

35. The system of claim 21, wherein the stem cells attached to the substrate surface are cultured to a population of at least $10^7$ cells within the chamber.

36. The system of claim 21, wherein the stem cells attached to the substrate surface are present within the chamber in a ratio to the lymphocytes of at least 1:10.

37. The system of claim 21, wherein the stem cells are cultured onto multiple substrate surface layers within the chamber.

38. The system of claim 21, wherein the system is a closed-loop system.

39. A method of inhibiting an autoimmune disorder due to autoreactive T cells, the method comprising:

extracting blood from a subject in need of treatment;

isolating lymphocytes from the extracted blood, thereby separating the lymphocytes from plasma;

exposing the isolated lymphocytes to stem cells such that regulatory T (Treg) cells are activated to suppress autoreactive T cells, wherein the stem cells are characterized by: (a) displaying embryonic stem cell characteristics; (b) displaying hematopoietic cell characteristics as being positive for leukocyte common antigen CD45; (c) not expressing the CD34 marker; (d) displaying low immunogenicity; and (e) expressing autoimmune regulator; and returning at least a portion of the lymphocytes to the subject.

40. The method of claim 39, wherein the autoimmune disorder is diabetes.

41. The method of claim 39, wherein the step of exposing the lymphocytes to stem cells further comprises:

culturing the stem cells in a reactor, and introducing the subject's lymphocytes into the reactor.

42. The method of claim 41, wherein the stem cells are allogenic stem cells to the lymphocytes.

43. The method of claim 41, wherein the stem cells are obtained from umbilical cord blood.

44. The method of claim 41, wherein the stem cells are obtained from peripheral blood.

45. The method of claim 44, wherein the stem cells are autologous stem cells obtained from a subject's own peripheral blood.

46. The method of claim 39, wherein the step of culturing the stem cells in the reactor further comprises:

collecting peripheral blood comprising peripheral blood mononuclear cells (PBMCs) and removing red blood cells from the PBMCs;

culturing the PBMCs in a low serum or serum-free culture medium in a non-tissue culture treated culture vessel, such that the PBMCs revert to embryonic-like stem cells, wherein the cell culture does not require a cell feeder;

isolating the embryonic-like stem cells; and attaching the embryonic-like stem cells to a surface of the reactor.

47. The method of claim 46, wherein the surface of the reactor has a net positive charge.

48. The method of claim 39, wherein the Treg cells are modulated by expression of a programmed death ligand 1 (PD-L1) by the stem cells.

49. The method of claim 39, wherein the Treg cells are activated by release of nitric oxide (NO) by the stem cells.

50. The method of claim 39, wherein the Treg cells are activated by cell-to-cell contact with the stem cells.

51. The method of claim 39, wherein the Treg cells are activated by soluble factors secreted by the stem cells within the reactor.

52. The method of claim 39, wherein the Treg cells are characterized by expression of the CD4, CD25, CD62L and CD69 markers.

53. The method of claim 39, wherein the steps of extracting blood and returning the treated lymphocytes to the subject are performed in a continuous manner.

54. The method of claim 39, wherein the subject's blood is continuously processed for a duration sufficient to extract at least 1 liter of the subject's blood.

* * * * *